(12) United States Patent
Fleβner et al.

(10) Patent No.: US 9,714,242 B2
(45) Date of Patent: *Jul. 25, 2017

(54) AZABICYCLIC CARBAMATES AND THEIR USE AS ALPHA-7 NICOTINIC ACETYLCHOLINE RECEPTOR AGONISTS

(71) Applicant: Bayer Intellectual Property GmbH, Monheim (DE)

(72) Inventors: Timo Fleβner, Wuppertal (DE); Frank-Gerhard Böβ, Frankfurt (DE); Christina Erb, Wiesbaden (DE); Frank-Thorsten Hafner, Wuppertal (DE); Katrin Schnizler, Rodenbach (DE); Dieter Lang, Velbert (DE); Joachim Luithle, Berlin (DE); Marja Van Kampen, Dusseldorf (DE); Franz-Josef Van Der Staay, Dronten (NL)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/299,750

(22) Filed: Jun. 9, 2014

(65) Prior Publication Data
US 2015/0065537 A1    Mar. 5, 2015

Related U.S. Application Data

(63) Continuation of application No. 13/441,407, filed on Apr. 6, 2012, now Pat. No. 8,772,511, which is a continuation of application No. 12/871,495, filed on Aug. 30, 2010, now Pat. No. 8,153,799, which is a continuation of application No. 10/522,611, filed as application No. PCT/EP03/07588 on Jul. 14, 2003, now Pat. No. 7,795,453.

(30) Foreign Application Priority Data

Jul. 29, 2002 (DE) .................................. 102 34 424

(51) Int. Cl.
C07D 453/02    (2006.01)

(52) U.S. Cl.
CPC .................................. C07D 453/02 (2013.01)

(58) Field of Classification Search
CPC .................................................. C07D 453/02
USPC ........................................................ 546/113
See application file for complete search history.

(56) References Cited

U.S. PATENT DOCUMENTS

| | | | |
|---|---|---|---|
| 4,605,652 A | 8/1986 | Welstead, Jr. | |
| 5,164,007 A | 11/1992 | Buxbaum | |
| 5,189,041 A | 2/1993 | Berger et al. | |
| 5,561,149 A | 10/1996 | Azria et al. | |
| 7,795,453 B2 * | 9/2010 | Fleβner et al. | 549/57 |
| 8,153,799 B2 * | 4/2012 | Flessner et al. | 546/133 |
| 8,772,511 B2 * | 7/2014 | Fleβner et al. | 549/57 |
| 9,108,961 B2 * | 8/2015 | Oliver-Shaffer | C07D 453/02 |
| 2002/0042428 A1 | 4/2002 | Myers et al. | |
| 2002/0091135 A1 | 7/2002 | Myers et al. | |
| 2003/0166654 A1 | 9/2003 | Nozulak | |
| 2004/0042429 A1 | 3/2004 | Kanterakis et al. | |

FOREIGN PATENT DOCUMENTS

| | | |
|---|---|---|
| AU | 3364693 A | 9/1993 |
| DE | 3724059 A1 | 2/1988 |
| EP | 372335 A2 | 6/1990 |
| EP | 485962 A2 | 5/1992 |
| JP | 2002030084 A | 1/2002 |
| WO | WO-93/15073 A1 | 8/1993 |
| WO | WO-01/85727 A1 | 11/2001 |
| WO | WO-02/15662 A2 | 2/2002 |
| WO | WO-03/055878 A1 | 7/2003 |

OTHER PUBLICATIONS

J-L. Galzi et al. "Neuronal Nicotinic Receptors: Molecular Organization and Regulations," Neuropharmacology, vol. 34, No. 6, 1995, pp. 563-582.
D. S. McGehee et al. "Physiological Diversity of Nicotinic Acetylcholine Receptors Expressed by Vertebrate Neurons," Annu. Rev. Physiol., vol. 57, 1995, pp. 521-546.
A. H. Rezvani et al. "Cognitive Effects of Nicotine," Biological Pshychiatry, vol. 49, 2001, pp. 258-267.
P. Seguela et al. "Molecular Cloning, Functional Properties, and Distribution of Rat Brain∝7: A Nicotinic Cation Channel Highly Permeable to Calcium," The Journal fo Neuroscience, vol. 13, No. 2, Feb. 1993, pp. 596-604.
R. S. Broide et al.: "The∝7 Nicotinic Acetylcholine Receptor in Neuronal Plasticity," Molecular Neurobiology, vol. 20, 1999, pp. 1-16.
D.P.N. Satchell et al. "Acylation by Ketens and Isocyanates. A Mechanistic Comparison" Chem. Soc. Rev. 4 (1975) 231-250.
T.P. Vishnyakova et al. "Substituted Ureas. Methods of Synthesis and Applications" Russ. Chem. Rev. 54 (1985) 249-261.
J.P. Wolfe et al. "An ammonia equivalent for the palladium-catalyzed amination of aryl halides and triflates" Tetrahedron Letters vol. 38, No. 36 (1997) 6367-6370.
J.H. Babler et al. "Non-catalyzed reductions with formate salts: conversion of nitroaromatic compounds to the corresponding primary amines" Synth. Commun. 11 (1981) 925-930.

(Continued)

*Primary Examiner* — Nizal Chandrakumar
(74) *Attorney, Agent, or Firm* — Morrison & Foerster LLP

(57) ABSTRACT

The invention relates to novel benzothiophene-, benzofuran-, and indole ureas and to the use thereof for producing medicaments for the treatment and/or prophylaxis of diseases and for improving perception, concentration, learning, and/or memory.

26 Claims, No Drawings

(56) References Cited

OTHER PUBLICATIONS

A.J. Bridges et al., "Fluorine as an ortho-Directing Group in Aromatic Metalation: A Two Step Preparation of Substituted Benzo[b]thiophene-2-carboxylates" Tetrahedron Letters vol. 33, No. 49 (1992) 7499-7502.
D. Bogdal et al., "Microwave-Assisted Preparation of Benzo[b]furans under Solventless Phase-Transfer Catalytic Conditions," Tetrahedron 56 (2000) 8769-8773.
D.A. Allen "Synthesis of indole-2-carboxylic acid esters" Synth. Commun. vol. 29, No. 3 (1999) 447-455.
C.W. Holzapfel et al. "Stille and suzuki cross coupling reactions of o-nitrophenyl triflates: A versatile route to a variety of deterocycles" Heterocycles vol. 48, No. 8 (1998) 1513-1518.
M. Akazome et al. "Palladium complex-catalyzed reductive n-heterocyclization of nitroarenes: Novel synthesis of indole and 2H-indazole derivatives" J. Org. Chem. 59 (1994) 3375-3380.
J.A. Valderrama et al. "Studies on Quinones. Part 30. Synthesis of Benzo[b]thiophene-4,7- quinones" Synth. Commun. vol. 27, No. 12 (1997) 2143-2157.
W.N. Lok et al. "Acetylenic Acids. II. The reaction of sulfur chlorides with phenylpropiolic acid and its methyl ester" Aust. J. Chem. 31 (1978) 605-616.
W. Ried et al. "Synthese von substituierten benzo[ b]thiophenen" Liebigs Ann. Chem. (1980) 1424-1427.
C.M. Bonnin et al. "Acetylenic acids. IV. The reactions of alkoxy-substituted phenylpropiolic acids and esters with sulfur halides, particularly thionly chloride" Aust. J. Chem. 32 (1979) 833-847.
V.P. Martin et al. "11. Synthese and eigenschaften der furo-und thieno-analogen von PQQ-triester" Helv. Chim Acta 77 (1994) 100-110.

A.J. Bridges et al. "Synthesis of [1]benzothieno[3,2-d]pyrimidines substituted with electron donating substituents on the benzene ring" J. Heterocyclic Chem. 34 (1997) 1163-1172.
J.R. Beck "Synthesis of Methyl 3-Hydroxybenzo[b]thiophene-2-carboxylate esters by nitro displacement" J. Org. Chem. vol. 38, No. 23 (1973) 4086-4087.
T.K. Shkinyova et al. "Regioselectivity of nucleophilic substitution of the nitro group in 2,4,6-trinitrobenzamide" Tetrahedron Letters 41 (2000) 4973-4975.
N. Choy et al. "An efficient one pot synthesis of n,n'-disubstituted unsymmetrical ureas and carbamates" Org. Prep. Proced. Int. vol. 28, No. 2 (1996) 173-177.
Characterisation of the binding of [$^3$H]methyllycaconitine: a new radioligand for labelling α7-type neuronal nicotinic acetylcholine receptors Neuropharmacology 38 (1999) 679-690.
A. Blokland, et al., "State-dependent impairment in object recognition after hippocampal NOS inhibition", NeuroReport vol. 8, No. 18 (Dec. 1998) 4205-4208.
A. Ennaceur et al., "A new one-trial test for neurobiological studies of memory in rats. 1: Behavioral data," Behavioural Brain Research, 31 (1988) 47-59.
A. Ennaceur et al., "Effects of physostigmine and scopolamine on rats' performances in object-recognition and radial-maze tests" Psychopharmacology 109 (1992) 321-330.
J. Prickaerts et al., "Possible role of nitric oxide-cyclic GMP pathway in object recognition memory: Effects of 7-nitroindazole and zaprinast", European Journal of Pharmacology 337 (1997) 125-136.

\* cited by examiner

AZABICYCLIC CARBAMATES AND THEIR USE AS ALPHA-7 NICOTINIC ACETYLCHOLINE RECEPTOR AGONISTS

CROSS REFERENCE TO RELATED APPLICATIONS

This application is a continuation of U.S. patent application Ser. No. 13/441,407, filed Apr. 6, 2012, which application is a continuation of U.S. patent application Ser. No. 12/871,495, filed Aug. 30, 2010, now U.S. Pat. No. 8,153,799, which is a continuation of U.S. patent application Ser. No. 10/522,611, filed Jan. 27, 2005, now U.S. Pat. No. 7,795,453, which is the U.S. National Stage application under 35 U.S.C. §371 of International Patent Application Serial No. PCT/EP2003/007588, filed Jul. 14, 2003, which claims the benefit of German Patent Application No. 10234424.8, filed Jul. 29, 2002, the disclosures of each of which are expressly incorporated by reference in their entireties.

The invention relates to novel benzothiophene-, benzofuran- and indoleureas, processes for their preparation, and their use for producing medicaments for the treatment and/or prophylaxis of diseases and for improving perception, concentration, learning and/or memory.

Nicotinic acetylcholine receptors (nAChR) form a large family of ion channels which are activated by the messenger acetylcholine which is produced in the body (Galzi et al., *Neuropharmacol*, 1995, 34, 563-582). A functional nAChR consists of five subunits which may be different (certain combinations of α1-9 and (β1-4,γ,δ,ε subUnits) or identical (α 7-9). This leads~to the formation of a diversity of subtypes which differ in the distribution in the muscles, the nervous system and other organs (McGehee et al, *Annu. Rev. Physiol*, 1995, 57, 521-546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani et al., *Biol. Psychiatry* 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Séguéla et al., *J. Neurosci,* 1993, 13, 596-604). The α7 nAChR has a particularly high permeability for calcium ions, increases glutamatergic neurotransmission, influences the growth of axons and, in this way, modulates neuronal plasticity (Broide et al., *Mol. Neurobiol*, 1999, 20, 1-16).

Certain N-(1-azabicyclo[2.2.2]oct-3-yl)heteroaryl carboxamides for the treatment of, inter alia, psychoses are described in DE-A 37 24 059.

N-(Azabicycloalkyl)heteroaryl carboxamides, in particular N-(1-azabicyclo[2.2.2]oct-4-yl)benzothiophene-3-carboxamides, are disclosed in WO 93/15073 and in EP-A 485 962 as intermediates for the synthesis of pharmaceutically active compounds.

U.S. Pat. No. 4,605,652 and EP-A 372 335 disclose, for example, N-(1-azabicyclo[2.2.2]oct-3-yl)thiophene-2-carboxamide and its memory-improving effect.

JP-A 14 030 084 describes 1-azabicycloalkanes for the treatment of, inter alia, dementia, attention deficit hyperactivity disorder and impairments of learning and memory.

The present invention relates to compounds of the formula

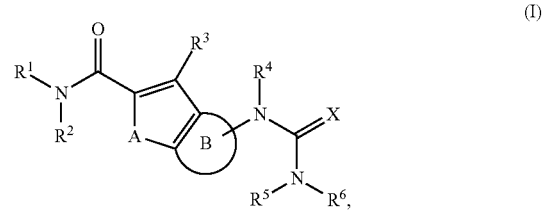

in which
$R^1$ is 1-azabicyclo[2.2.2]oct-3-yl,
$R^2$ is hydrogen or $C_1$-$C_6$-alkyl,
$R^3$ is hydrogen, halogen, amino, hydroxy or $C_1$-$C_6$-alkyl,
$R^4$ is hydrogen, $C_1$-$C_6$-alkyl which is optionally substituted by a radical selected from the group of hydroxy, halogen, cyano, $C_1$-$C_6$-alkoxy, trifluoromethyl, trifluoromethoxy,
$R^5$ is hydrogen or $C_1$-$C_6$-alkyl, or
$R^4$ and $R^5$ together with the nitrogen atom to which they are bonded are a 5- to 6-membered heterocycle which is optionally substituted by up to 2 substituents independently of one another selected from the group of $C_1$-$C_6$-alkyl, $C_1$-$C_4$-acyl, oxo, thioxo,
$R^6$ is (i) hydrogen, (ii) $C_1$-$C_6$-alkyl, (iii) $C_3$-$C_8$-cycloalkyl, (iv) $C_6$-$C_{10}$-aryl, (v) 5- to 10-membered heteroaryl, (vi) $C_6$-$C_{10}$-arylcarbonyl, where (ii) is optionally substituted by phenyl, $C_1$-$C_6$-alkoxycarbonyl or $C_1$-$C_6$-alkoxy, and (iv), (v) and (vi) are optionally substituted by up to 3 radicals selected independently of one another from the group of $C_1$-$C_6$-alkyl, $C_1$-$C_6$-hydroxyalkyl, 3- to 8-membered heterocyclyl, $C_6$-$C_{10}$-aryl, 5- to 10-membered heteroaryl, hydroxy, halogen, cyano, $C_1$-$C_6$-alkoxy, $C_1$-$C_6$-acyl, trifluoromethyl, trifluoromethoxy, nitro, amino, $C_1$-$C_6$-alkylamino, $C_1$-$C_6$-acylamino, or
$R^5$ and $R^6$ together with the nitrogen atom to which they are bonded are a 3- to 10-membered heterocycle which is optionally substituted by $C_1$-$C_6$-alkyl or $C_1$-$C_6$-hydroxyalkyl,
A is oxygen, nitrogen or sulfur,
X is oxygen or sulfur,
the ring B is benzo or pyrido, each of which are optionally substituted by radicals from the series halogen, cyano, trifluoromethyl, trifluoromethoxy, nitro, amino, $C_1$-$C_6$-alkyl and $C_1$-$C_6$-alkoxy,
and the solvates, salts or solvates of the salts of these compounds.

Solvates is the term used for the purposes of the invention for those forms of the compounds which form a complex with solvent molecules by coordination in the solid or liquid state. Hydrates are a special form of solvates in which the coordination takes place with water.

Salts which are preferred for the purposes of the invention are physiologically acceptable salts of the compounds of the invention.

Physiologically acceptable salts of the compounds (I) may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

However, physiologically acceptable salts of the compounds (I) are also salts with conventional bases, such as, for example, alkali metal salts (e.g. sodium or potassium salts), alkaline earth metal salts (e.g. calcium or magnesium salts) or ammonium salts derived from ammonia or organic amines such as, for example, diethylamine, triethylamine, ethyldiisopropylamine, procaine, dibenzylamine, N-methylmorpholine, dihydroabiethylamine, 1-ephenamine or methylpiperidine.

The compounds of the invention may exist in stereoisomeric forms (enantiomers, diastereomers). The invention therefore relates both to the enantiomers or diastereomers and to respective mixtures thereof. These enantiomer and diastereomer mixtures can be separated in a known manner into the stereoisomerically pure constituents.

For the purposes of the present invention, the substituents generally have the following meaning:

$C_1$-$C_6$-alkoxy is a straight-chain or branched alkoxy radical having 1 to 6, preferably 1 to 4, particularly preferably 1 to 3, carbon atoms. Nonlimiting examples include methoxy, ethoxy, n-propoxy, isopropoxy, tert-butoxy, n-pentoxy and n-hexoxy.

$C_1$-$C_6$-alkoxycarbonyl is a straight-chain or branched alkoxy carbonyl radical having 1 to 6, preferably 1 to 4 and particularly preferably 1 to 3, carbon atoms. Nonlimiting examples include methoxycarbonyl, ethoxycarbonyl, n-propoxycarbonyl, isopropoxycarbonyl and tert-butoxycarbonyl.

$C_1$-$C_6$-alkyl is a straight-chain or branched alkyl radical having 1 to 6, preferably 1 to 4, particularly preferably 1 to 3, carbon atoms. Nonlimiting examples include methyl, ethyl, n-propyl, isopropyl, tert-butyl, n-pentyl and n-hexyl.

$C_1$-$C_6$-acyl is a straight-chain or branched acyl radical having 1 to 6, preferably 1 to 4, carbon atoms. Nonlimiting examples include acetyl, ethylcarbonyl, propylcarbonyl, isopropylcarbonyl, butylcarbonyl, isobutylcarbonyl, pentylcarbonyl and hexylcarbonyl. Acetyl and ethylcarbonyl are preferred.

$C_3$-$C_8$-cycloalkyl is cyclopropyl, cyclopentyl, cyclobutyl, cyclohexyl, cycloheptyl or cyclooctyl. Those which may be mentioned as preferred are: cyclopropyl, cyclopentyl and cyclohexyl.

$C_1$-$C_6$-acylamino is an amino group having a straight-chain or branched alkanoyl substituent which has 1 to 6 carbon atoms and is linked via the carbonyl group. An acylamino radical having 1 to 2 carbon atoms is preferred. Nonlimiting examples include formamido, acetamido, propionamido, n-butyramido and pivaloylamido.

$C_1$-$C_6$-alkylamino is a straight-chain or branched mono- or dialkylamino radical having 1 to 6 carbon atoms. Preference is given to a straight-chain or branched alkylamino radical having 1 to 4, particularly preferably having 1 to 3, carbon atoms. Nonlimiting examples include methylamino, ethylamino, n-propylamino, isopropylamino, tert-butylamino, n-pentylamino and n-hexylamino, dimethylamino, diethylamino, di-n-propylamino, diisopropylamino, di-t-butylamino, di-n-pentylamino, di-n-hexylamino, ethylmethylamino, isopropylmethylamino, n-butylethylamino, n-hexyl-i-pentylamino.

$C_1$-$C_6$-hydroxyalkyl is a straight-chain or branched hydroxyalkyl radical having 1 to 6 carbon atoms which is linked via the alkyl group. Preference is given to a straight-chain or branched hydroxyalkyl radical having 1 to 4, particularly preferably having 1 to 3, carbon atoms. Nonlimiting examples include hydroxymethyl, hydroxyethyl, 3-hydroxypropyl, hydroxyisopropyl, hydroxy-tert-butyl, 5-hydroxypentyl and 6-hydroxyhexyl.

3- to 8-membered heterocyclyl is a cycloalkyl group having 3 to 8, preferably 5 to 7, carbon atoms, with up to 2 ring carbon atoms in the cycloalkyl group having been replaced by a nitrogen atom and/or a further heteroatom selected from the group of nitrogen, oxygen or sulfur, and the radical is attached via one of the ring nitrogen atoms. Examples which may be mentioned as preferred are pyrazolidin-1-yl, piperazin-1-yl, perhydro-1,4-diazepin-1-yl, morpholin-1-yl, thiomorpholin-1-yl, piperidin-1-yl.

3- to 10-membered heterocyclyl is a mono- or bicyclic cycloalkyl group having 3 to 10, preferably 5 to 8, carbon atoms, with up to 2 ring carbon atoms in the cycloalkyl group having been replaced by a nitrogen atom and/or a further heteroatom selected from the group of nitrogen, oxygen or sulfur, and the radical is attached via one of the ring nitrogen atoms. Examples which may be mentioned as preferred are: pyrazolidin-1-yl, piperazin-1-yl, perhydro-1,4-diazepin-1-yl, morpholin-1-yl, thiomorpholin-1-yl, piperidin-1-yl, azabicyclo[3.2.0]heptyl, azabicyclo[3.2.1]heptyl, azabicyclo[3.2.2]heptyl, azabicyclo[3.2.1]octyl, azabicyclo[3,2,2]octyl.

$C_6$-$C_{10}$-aryl is a mono- or bicyclic aromatic, carbocyclic radical usually having 6 to 10 carbon ring atoms. Nonlimiting examples include phenyl and naphthyl.

$C_6$-$C_{10}$-arylcarbonyl is a mono- or bicyclic arylcarbonyl radical usually having 6 to 10 carbon ring atoms. Nonlimiting examples include phenylcarbanyl and naphthylcarbonyl.

5- to 10-membered heteroaryl is an aromatic mono- or bicyclic radical usually having 5 to 10, preferably 5 to 6, ring atoms and up to 5, preferably up to 4, hetero ring atoms from the series S, O and N. Nonlimiting examples include thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Halogen is fluorine, chlorine, bromine and iodine. Fluorine, chlorine and bromine are preferred, and fluorine and chlorine are particularly preferred.

When radicals in the compounds of the invention are optionally substituted, unless indicated otherwise the radicals may have one or more identical or different substituents.

Preference is given to compounds of the formula (I), in which $R^1$ is 1-azabicyclo[2.2.2]oct-3-yl, $R^2$ is hydrogen or $C_1$-$C_4$-alkyl, $R^3$ is hydrogen, halogen, amino, hydroxy or $C_1$-$C_4$-alkyl, $R^4$ is hydrogen or $C_1$-$C_4$-alkyl which is optionally substituted by a radical selected from the group of hydroxy, $C_1$-$C_3$-alkoxy, trifluoromethyl, trifluoromethoxy, $R^5$ is hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_6$-alkyl, $C_1$-$C_4$-acyl, oxo, thioxo, $R^6$ is (i) hydrogen, (ii) $C_1$-$C_4$-alkyl, (iii) $C_5$-$C_6$-cycloalkyl, (iv) phenyl, (v) 5- to 6-membered heteroaryl, where (ii) is optionally substituted by phenyl, and (iv) and (v) are optionally substituted by up to 3 radicals selected independently of one another from the group of $C_1$-$C_4$-alkyl, $C_1$-$C_4$-hydroxyalkyl, hydroxy, chlorine, fluorine, cyano, $C_1$-$C_3$-alkoxy, $C_1$-$C_6$-acyl, trifluoromethyl, trifluoromethoxy, amino, $C_1$-$C_3$-alkylamino, $C_1$-$C_3$-acylamino, or $R^5$ and $R^6$ together with the nitrogen atom to which they are bonded are a 5- to 6-membered heterocycle which is optionally substituted by $C_1$-$C_3$-alkyl or $C_1$-$C_3$-hydroxyalkyl, A is oxygen, nitrogen or sulfur, X is oxygen and the ring B is benzo or pyrido, each of which are optionally substituted by radicals from the series chlorine, fluorine, cyano, trifluoromethyl, trifluoromethoxy, amino, $C_1$-$C_4$-alkyl and $C_1$-$C_4$-alkoxy, and the solvates, salts or solvates of the salts of these compounds.

Preference is likewise given to compounds of the formula (I) in which $R^1$ is 1-aza-bicyclo[2.2.2]oct-3-yl, $R^2$ is hydrogen or $C_1$-$C_4$-alkyl, $R^3$ is hydrogen, halogen, amino, hydroxy or $C_1$-$C_4$-alkyl, $R^4$ is hydrogen, $C_1$-$C_4$-alkyl which is optionally substituted by a radical selected from the group of hydroxy, halogen, cyano, trifluoromethyl, trifluoromethoxy, $R^5$ is hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_6$-alkyl, $C_1$-$C_4$-acyl, oxo, thioxo, $R^6$ is (i) hydrogen, (ii) $C_1$-$C_4$-alkyl, (iii) $C_5$-$C_6$-cycloalkyl, (iv) phenyl, (v) 5- to 6-membered heteroaryl, (vi) $C_6$-$C_{10}$-arylcarbonyl, where (ii) is optionally substituted by phenyl, $C_1$-$C_4$-alkoxycarbonyl or $C_1$-$C_3$-alkoxy, and (iv), (v) and (vi) are optionally substituted by up to 3 radicals selected independently of one another from the group of $C_1$-$C_4$-alkyl, $C_1$-$C_4$-hydroxyalkyl, 3- to 8-membered heterocyclyl, $C_6$-$C_{10}$-aryl, 5- to 10-membered heteroaryl, hydroxy, fluorine, chlorine, cyano, $C_1$-$C_3$-alkoxy, $C_1$-$C_3$-acyl, trifluoromethyl, trifluoromethoxy, nitro, amino, $C_1$-$C_3$-alkylamino, $C_1$-$C_3$-acylamino, or $R^5$ and $R^6$ together with the nitrogen atom to which they are bonded are a 3- to 10-membered heterocycle which is optionally substituted by $C_1$-$C_3$-alkyl or $C_1$-$C_3$-hydroxyalkyl, A is oxygen or sulfur, X is oxygen, the ring B is benzo or pyrido, each of which are optionally substituted by radicals from the series chlorine, fluorine, cyano, trifluoromethyl, trifluoromethoxy, amino, $C_1$-$C_4$-alkyl and $C_1$-$C_4$-alkoxy, and the solvates, salts or solvates of the salts of these compounds.

Preference is likewise given to compounds of the formula (I) in which $R^1$ is 1-azabicyclo[2.2.2]oct-3-yl, $R^2$ is hydrogen, $R^3$ is hydrogen, chlorine, fluorine, amino or $C_1$-$C_3$-alkyl, $R^4$ is hydrogen, methyl or ethyl, where methyl and ethyl are optionally substituted by a radical selected from the group of hydroxy, methoxy, ethoxy, trifluoromethyl, trifluoromethoxy, or $R^4$ and $R^5$ together with the nitrogen atom to which they are bonded are a 5- to 6-membered heterocycle which is optionally substituted by up to 2 substituents independently of one another selected from the group of $C_1$-$C_3$-alkyl, $C_1$-$C_4$-acyl, oxo, thioxo, $R^5$ is hydrogen or $C_1$-$C_3$-alkyl, $R^6$ (i) hydrogen, (ii) $C_1$-$C_4$-alkyl, (iii) cyclopentyl, cyclohexyl, (iv) phenyl, (v) benzyl, (vi) phenethyl, where (iv) to (vi) are optionally substituted by up to 3 radicals selected independently of one another from the group of hydroxy, chlorine, fluorine, cyano, methoxy, ethoxy, $C_1$-$C_4$-acyl, trifluoromethyl, trifluoromethoxy, amino, $C_1$-$C_3$-alkylamino, A is oxygen or sulfur, X is oxygen and the ring B is benzo which is optionally substituted by radicals from the series chlorine, fluorine, cyano, trifluoromethyl, trifluoromethoxy, $C_1$-$C_4$-alkyl, methoxy and ethoxy, and the solvates, salts or solvates of the salts of these compounds.

Preference is likewise given to compounds of the formula (I) in which $R^1$ is 1-azabicyclo[2.2.2]oct-3-yl, $R^2$ to $R^4$ are hydrogen, $R^5$ is hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_4$-alkyl, $C_1$-$C_4$-acyl, oxo, thioxo, $R^6$ is (i) hydrogen, (ii) $C_1$-$C_4$-alkyl, (iii) $C_5$-$C_6$-cycloalkyl, (iv) phenyl, (v) pyridyl, (vi) $C_6$-$C_{10}$-arylcarbonyl, where (ii) is optionally substituted by phenyl, $C_1$-$C_4$-alkoxycarbonyl or $C_1$-$C_3$-alkoxy, and (iv), (v) and (vi) are optionally substituted by up to 3 radicals selected independently of one another from the group of $C_1$-$C_4$-alkyl, $C_1$-$C_4$-hydroxyalkyl, 3- to 8-membered heterocyclyl, $C_6$-$C_{10}$-aryl, 5- to 10-membered heteroaryl, hydroxy, fluorine, chlorine, cyano, $C_1$-$C_3$-alkoxy, $C_1$-$C_3$-acyl, trifluoromethyl, trifluoromethoxy, nitro, amino, $C_1$-$C_3$-alkylamino, $C_1$-$C_3$-acylamino, or $R^5$ and $R^6$ together with the nitrogen atom to which they are bonded are a 3- to 10-membered heterocycle which is optionally substituted by $C_1$-$C_3$-alkyl or $C_1$-$C_3$-hydroxyalkyl, A is oxygen or sulfur, X is oxygen, the ring B is benzo, and the solvates, salts or solvates of the salts of these compounds.

Preference is likewise given to compounds of the formula

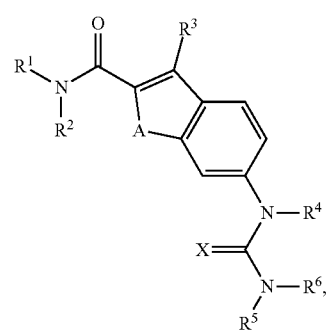

(Ia)

in which $R^1$ to $R^6$, A and X have the meanings indicated above, and the solvates, salts or solvates of the salts of these compounds.

Preference is likewise given to compounds of the formula

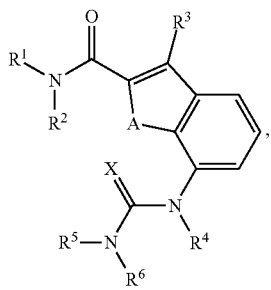

in which $R^1$ to $R^6$, A and X have the meanings indicated above, and the solvates, salts or solvates of the salts of these compounds.

Preference is likewise given to compounds of the formula

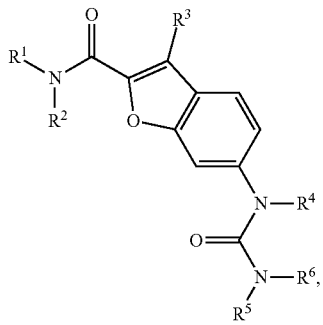

in which $R^1$ to $R^6$ have the meanings indicated in claims 1 to 6, and the solvates, salts or solvates of the salts of these compounds.

Preference is likewise given to compounds of the formula

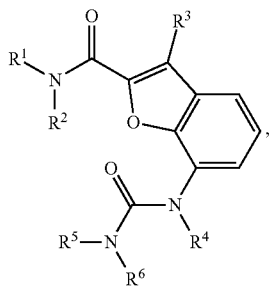

in which $R^1$ to $R^6$ have the meanings indicated in claims 1 to 6, and the solvates, salts or solvates of the salts of these compounds.

Preference is likewise given to compounds of the formulae (Ia) and (Ib) in which $R^1$ to $R^6$ have the meanings indicated above, and A and X are oxygen, and the solvates, salts or solvates of the salts of these compounds.

Preference is likewise given to compounds of the formulae (I) in which $R^1$ is (3R)-1-azabicyclo[2.2.2]oct-2-yl, and $R^2$ to $R^6$, A, X and the ring B have the meanings indicated above, and the solvates, salts or solvates of the salts of these compounds.

Preference is likewise given to compounds of the formula (I) in which $R^3$ is hydrogen, and $R^1$, $R^3$ to $R^6$, A, X and the ring B have the meanings indicated above, and the solvates, salts or solvates of the salts of these compounds.

Preference is likewise given to compounds of the formula (I) in which $R^3$ is hydrogen, fluorine or methyl, and $R^1$, $R^2$, $R^4$ to $R^6$, A, X and the ring B have the meanings indicated above, and the solvates, salts or solvates of the salts of these compounds.

Preference is likewise given to compounds of the formula (I) in which $R^3$ is hydrogen, chlorine or methyl, and $R^1$, $R^2$, $R^4$ to $R^6$, A, X and the ring B have the meanings indicated above, and the solvates, salts or solvates of the salts of these compounds.

Preference is likewise given to compounds of the formula (I) in which $R^3$ is hydrogen, and $R^1$, $R^2$, $R^4$ to $R^6$, A, X and the ring B have the meanings indicated above, and the solvates, salts or solvates of the salts of these compounds.

Preference is likewise given to compounds of the formula (I) in which $R^4$ is hydrogen or $C_1$-$C_6$-alkyl which is optionally substituted by a radical selected from the group of hydroxy, $C_1$-$C_6$-alkoxy, trifluoromethyl, trifluoromethoxy, and $R^1$ to $R^3$, $R^5$, $R^6$, A, X and the ring B have the meanings indicated above, and the solvates, salts or solvates of the salts of these compounds.

Particular preference is given to compounds of the formula (I) in which $R^4$ is hydrogen, methyl or ethyl, where methyl and ethyl is optionally substituted by a radical selected from the group of hydroxy, methoxy, ethoxy, trifluoromethyl, trifluoromethoxy, and $R^1$ to $R^3$, $R^5$, $R^6$, A, X and the ring B have the meanings indicated above, and the solvates, salts or solvates of the salts of these compounds.

Preference is likewise given to compounds of the formula (I) in which $R^5$ is hydrogen, and $R^1$ to $R^4$, $R^6$, A, X and the ring B have the meanings indicated above, and the solvates, salts or solvates of the salts of these compounds.

Preference is likewise given to compounds of the formula (I) in which X is an oxygen atom, and $R^1$ to $R^6$, A and the ring B have the meanings indicated above, and the solvates, salts or solvates of the salts of these compounds.

Preference is likewise given to compounds of the formula (I) in which A is an oxygen atom, and $R^1$ to $R^6$, X and the ring B have the meanings indicated above, and the solvates, salts or solvates of the salts of these compounds.

Preference is likewise given to compounds of the formula (I) in which the ring B is benzo which is optionally substituted by 1 to 3 radicals from the series halogen, cyano, trifluoromethyl, trifluoromethoxy and $C_1$-$C_4$-alkyl, and $R^1$ to $R^6$, A and X have the meanings indicated above, and the solvates, salts or solvates of the salts of these compounds.

Very particular preference is given to combinations of two or more of the preferred ranges mentioned above.

The invention further relates to process for preparing the compounds of the invention, in which compounds of the formula

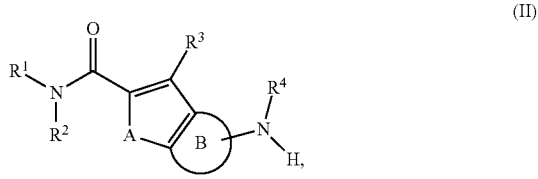

in which

R$^1$ to R$^4$, A and B have the abovementioned meanings, are reacted with compounds of the formula

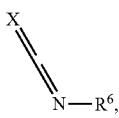
(III)

in which

X and R$^6$ have the abovementioned meanings, and the resulting compounds (I) are reacted where appropriate with the appropriate (a) solvents and/or (b) bases or acids to give the solvates, salts or solvates of the salts thereof.

The reaction can take place in inert solvents, where appropriate in the presence of a base, preferably in a temperature range from 20° C. to 60° C. under atmospheric pressure.

Examples of inert solvents are halohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, glycol dimethyl ether or diethylene glycol dimethyl ether, hydrocarbons such as benzene, xylene, toluene, hexane, cyclohexane or petroleum fractions, nitroalkanes such as nitromethane, carboxylic esters such as ethyl acetate, ketones such as acetone or 2-butanone, optionally N-alkylated carboxamides, such as dimethylformamide or dimethylacetamide, alkyl sulfoxides such as dimethyl sulfoxide, carbonitriles such as acetonitrile or heteroaromatic compounds such as pyridine. Dimethylformamide or tetrahydrofuran are preferred.

Examples of bases are alkali metal hydroxides such as sodium or potassium hydroxide, alkali metal carbonates and bicarbonates such as cesium carbonate, sodium bicarbonate, sodium or potassium carbonate, or amides such as lithium diisopropylamide, alkylamines such as triethylamine, diisopropylethylamine or DBU, preferably diisopropylethylamine or triethylamine.

Synthesis of compounds (I) can take place according to Satchel, *Chem, Soc. Rev.* 1975, 4, 231-250 or Glebova, *Russ. Chem. Rev.* 1985, 54, 249-261.

Compounds (II) can be synthesized by known processes from the appropriate bromo- or nitro-substituted precursors. Thus, they can be synthesized for example from the bromo-substituted aromatic compounds by palladium-catalyzed reactions for example according to J. P. Wolfe et al., *Tetrahedron Lett.* 1997, 38, 6367-6370.

The nitro group of the nitro-substituted precursors can be reduced by catalytic hydrogenation, for example according to Rylander, *Hydrogenation Methods*, Academic Press: New York, 1967 or Babler, Sarussi, *Synth. Commun.* 1981, 11, 925.

The invention further relates to the process for preparing the compounds of the formula

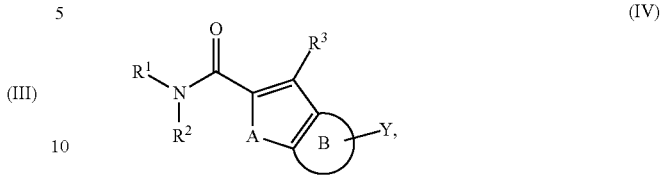
(IV)

in which

R$^1$ to R$^3$, A and the ring B have the abovementioned meanings, and

Y is bromine, nitro or —NH(PG), where PG is a protective group for the amino function, for example tert-butyloxycarbonyl or benzyloxycarbonyl, characterized in that compounds of the formula

R$^1$R$^2$NH (V), in which R$^1$ and R$^2$ have the abovementioned meanings, are reacted with a compound of the formula

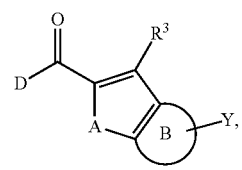
(VI)

in which R$^3$, A and the ring B have the abovementioned meanings, and

D is hydroxy, halogen, mesyloxy or isobutyloxycarbonyloxy, preferably hydroxy and chlorine.

The reaction can take place in inert solvents, where appropriate in the presence of a base and/or of a condensing agent, preferably in a temperature range from 0° C. to 50° C. under atmospheric pressure.

Preferred inert solvents include dioxane, dimethylformamide and methylene chloride.

Examples of bases are alkali metal hydroxides such as sodium or potassium hydroxide, alkali metal carbonates and bicarbonates such as cesium carbonate, sodium bicarbonate, sodium or potassium carbonate, or amides such as lithium diisopropylamide, alkylamines such as triethylamine, diisopropylethylamine or DBU, preferably diisopropylethylamine or triethylamine and DBU.

Condensing agents for the purposes of the invention are, for example, carbodiimides such as, for example, N,N'-diethyl-, N,N'-dipropyl-, N,N'-dicyclo-hexylcarbodiimide, N-(3-dimethylaminoisopropyl)-N-ethylcarbodiimide hydrochloride (EDC), N-cyclohexylcarbodiimide-M-propyloxymethylpolystyrene (PS-carbodiimide); carbonyl compounds such as carbonyldiimidazote; 1,2-oxazolium compounds such as 2-ethyl-5-phenyl-1,2-oxazolium-3-sulfate or 2-tert-butyl-5-methylisoxazolium perchlorate; acylamino compounds such as 2-ethoxy-1-ethoxycarbonyl-1,2-dihydroquinoline; in addition propanephosphonic anhydride, isobutyl chloroformate, bis(2-oxo-3-oxazolidinyl)phosphoryl chloride, benzotriazolyloxy-tri(dimethylamino)phosphonium hexafluorophosphate, O-(benzotriazol-1-yl)-N,N,N',N'-tetramethyltuonium hexafluorophosphate (HBTU), 2-(2-oxo-1-(2H)-pyridyl)-1,1,3,3-tetramethyluronium tetrafluoroborate (TPTU), O-(7-azabenzotriazol-1-yl)-N,N,N',N'-tetramethyluronium hexafluorophosphate (HATU), benzotriazol-1-yloxytris(dimethylamino)phosphonium hexafluorophosphate (BOP), and mixtures thereof.

It may be advantageous where appropriate to use the condensing agent in the presence of an auxiliary nucleophile such as, for example, 1-hydroxybenzotriazole (HOBt).

Particular preference is given to the combination of N-(3-dimethylaminoisopropyl)-N'-ethylcarbodiimide hydrochloride (EDC), 1-hydroxybenzotriazole (HOBt) and triethylamine in dimethylformamide or of O-(7-azabenzotriazol-1-yl)-N,N,N',N'-tetramethyluronium hexafluorophosphate (HATU) and diisopropylethylamine in dimethylformamide.

The compounds (V) and (IV) are known or can be synthesized in analogy to known processes from the appropriate precursors (cf., for example, "Comprehensive Heterocyclic Chemistry", Katritzki et al., editors; Elsevier, 1996). Thus, for example, substituted benzothiophene-2-carboxylic acids can be obtained from appropriately substituted 2-halobenzaldehydes by reaction with methyl mercaptoacetate (see, for example, A. J. Bridges et al., Tetrahedron Lett. 1992, 33, 7499) and subsequent hydrolysis of the ester:

Derivatives of indole-2-carboxylic acids can be prepared by known processes: D. A. Allen, Synth. Commun. 1999, 29, 447; C. W. Holzapfel, C. Dwyer, Heterocycles 1998, 48, 1513; M. Akazome et al., J. Org. Chem. 1994, 59, 3375.

The radical $R^3$ can be introduced for example by reacting suitably substituted ketones with methyl mercaptoacetate in accordance with synthesis scheme 1 (J. A. Valderama, C. Valderama, Synth. Commun, 1997, 27, 2143). Further methods for introducing halogen, amino or hydroxy at this position are known from the literature: W. N. Lok, A. D. Ward, Aust. J. Chem. 1978, 31, 605; W. Reid et al., Liebigs Ann. Chem, 1980, 1424; C. M. Bonnin et al., Aust. J. Chem. 1979, 32, 883; P. Martin, T. Winkler, Helv. Chim, Acta 1994, 77, 100; A. J. Bridges, H. Zhou, J. Heterocycl. Chem. 1997, 34, 1163; J. R. Beck, J. Org. Chem. 1973, 38, 4086; T. K. Shkintova et al., Tetrahedron Lett. 2000, 41, 4973

Synthesis of the corresponding pyrido derivatives is possible starting from 2-halobenzonitriles by reacting with methyl mercaptoacetate to give the 3-aminobenzo-thiophene-2-carboxylic esters:

Synthesis scheme 1:

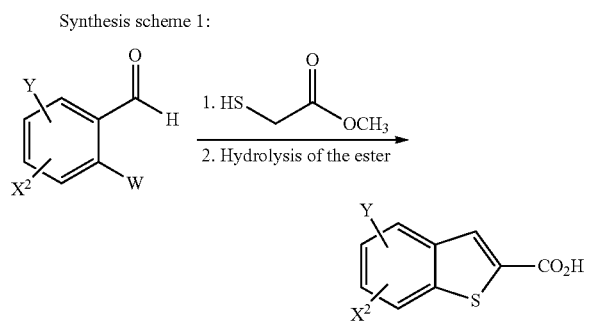

W = F, Cl, Br, NO2
$X^2$ = halogen, cyano, trifluoromethyl, trifluoromethoxy, nitro, amino, $C_1$-$C_8$-alkyl and $C_1$-$C_8$-alkoxy Synthesis scheme 2:

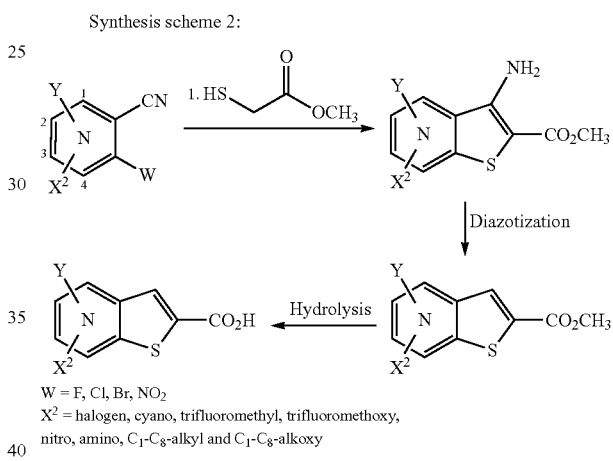

W = F, Cl, Br, $NO_2$
$X^2$ = halogen, cyano, trifluoromethyl, trifluoromethoxy, nitro, amino, $C_1$-$C_8$-alkyl and $C_1$-$C_8$-alkoxy The corresponding pyrido derivatives can be synthesized starting from 2-halobenzonitriles by reaction with methyl mercaptoacetate to give the 3-amino-benzothiophene-2-carboxylic esters:

Substituted benzofuran-2-carboxylic acids can be obtained for example as described by D. Bogdal et al., Tetrahedron 2000, 56, 8769.

The nitrogen atom shown in the ring may replace a CH group at one of positions 1 to 4 in the aromatic system.

The amino function can be removed by diazotization. Finally, the ester can be hydrolyzed to give the target compound.

The process described above can be illustrated by way of example via the following formula diagram:

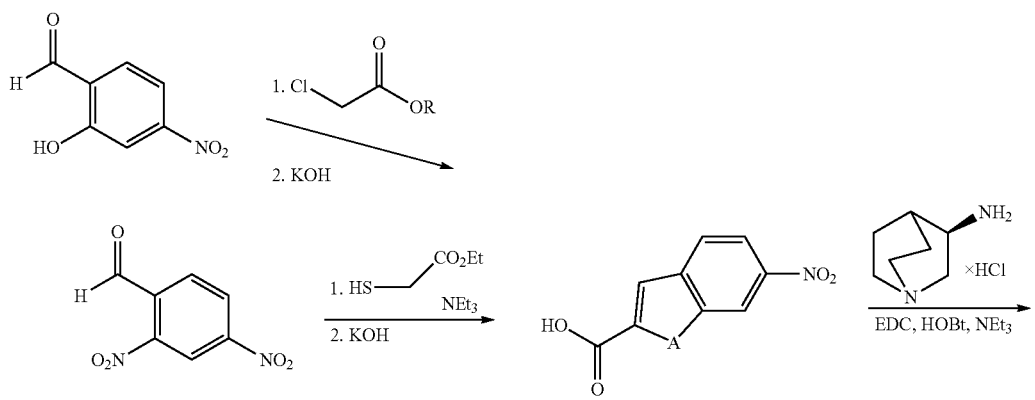

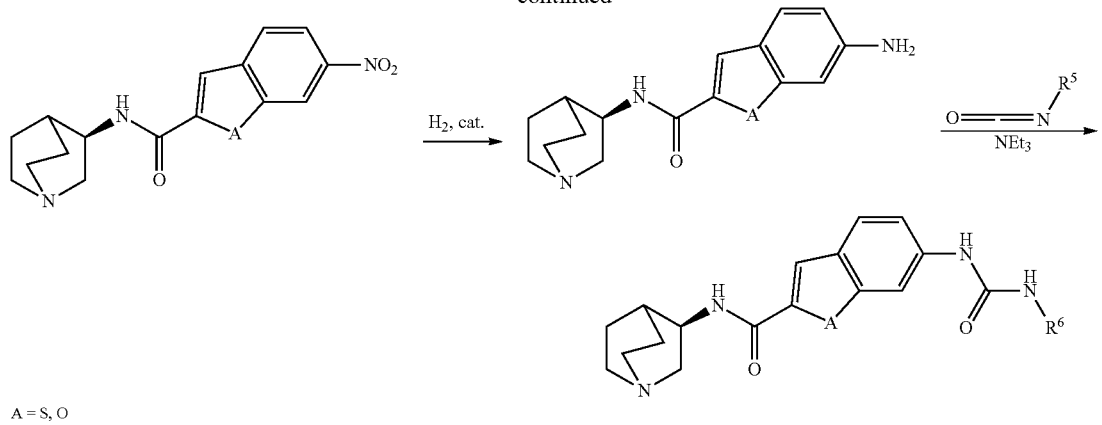

A = S, O

Modification of the last step as shown in the following scheme makes it possible to synthesize trisubstituted ureas where $R^5$ and $R^6$ may form with the nitrogen atom to which they are bonded a heterocycle.

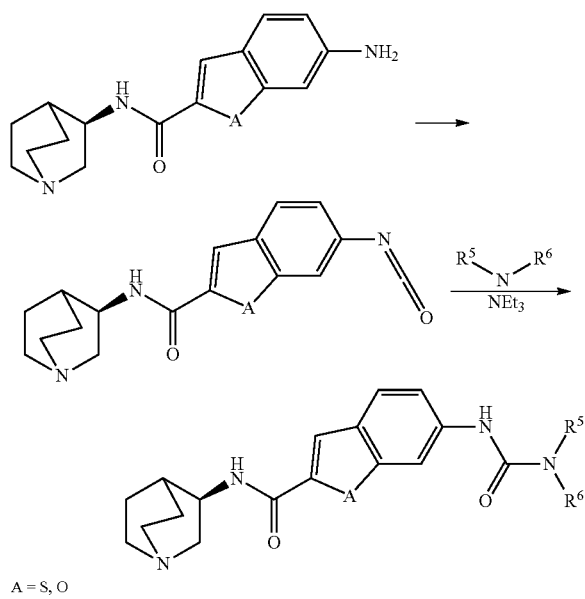

A = S, O

A further possibility is to obtain asymmetrically substituted ureas also by using suitable phosgene derivatives such as, for example, p-nitrophenyl chloroformate (cf.: N. Choy et al., Org. Prep. Proced. Int. 1996, 28, 173), starting from variously substituted amines.

The compounds of the invention are suitable for use as medicaments for the treatment and/or prophylaxis of diseases in humans and animals.

They act as α7 nAChR agonists and show a valuable range of pharmacological effects which could not have been predicted.

The compounds of the invention can, because of their pharmacological properties, be employed alone or in combination with other active ingredients for the treatment and/or prevention of cognitive impairments, especially of Alzheimer's disease. Because of their selective effect as α7 nAChR agonists, they are particularly suitable for improving perception, concentration, learning or memory, especially after cognitive impairments like those occurring for example in mild cognitive impairment, age-associated learning and memory impairments, age-associated memory loss, vascular dementia, craniocerebral trauma, stroke, dementia occurring after strokes (post-stroke dementia), post-traumatic craniocerebral trauma, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, progressive nuclear palsy, dementia with corticobasal degeneration, amyotrophic lateral sclerosis (ALS), Huntington's disease, multiple sclerosis, thalamic degeneration, Creutzfeld-Jacob dementia, HIV dementia, schizophrenia, schizophrenia with dementia or Korsakoffs psychosis.

The compounds of the invention can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", 2nd edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache (low back pain) or rheumatic pain. In addition, these active ingredients are also suitable for the therapy of primary acute pain of any origin and of secondary states of pain resulting therefrom, and for the therapy of states of pain which were formerly acute and have become chronic. The compounds of the invention can be employed alone or in combination with other active ingredients for the treatment of schizophrenia.

The in vitro effect of the compounds of the invention can be shown in the following assays:

1. Determination of the affinity of test substances for α7 UAChR by inhibition of [$^3$H]-methyllycaconitine binding to rat brain membranes The [$^3$H]-methyllycaconitine binding assay is a modification of the method described by Davies et al. in Neuropharmacol, 1999, 38, 679-690.

Rat brain tissue (hippocampus or whole brain) is homogenized in aqueous homogenization buffer (10% w/v, 0.32 M sucrose, 1 mM EDTA, 0.1 mM phenylmethylsulfonyl fluoride (PMSF), 0.01% (w/v) $NaN_3$, pH 7.4, 4° C.) at 600 rpm in a glass homogenizer. The homogenate is centrifuged (1000×g, 4° C., 10 min) and the supernatant is removed. The pellet is resuspended (20% w/v) and the suspension is centrifuged (1000×g, 4° C., 10 min). The two supernatants are combined and centrifuged (15 000×g, 4° C., 30 min). The pellet obtained in this way is referred to as the P2 fraction.

The P2 pellet is suspended in binding buffer (50 mM Tris-HCl, 1 mM $MgCl_2$, 120 mM NaCl, 5 mM KCl, 2 mM $CaCl_2$, pH 7.4), and the suspension is centrifuged (15 000×g, 4° C., 30 min), twice.

The residue is resuspended in binding buffer to a concentration of 4 mg/ml and incubated in a volume of 250 µl (amount of membrane protein 0.4 mg) in the presence of 2 nM [3H]-methyllycaconitine, 0.1% (w/v) BSA (bovine serum albumin) and various concentrations of the test substance at 21° C. for 60 min.

Incubation is then carried out in the presence of 1 µM α-bungarotoxin or 100 µM nicotine or 10 µM MLA (methyllycaconitine). The incubation is stopped by adding 4 ml of PBS (20 mM $Na_2HPO_4$, 5 mM $KH_2PO_4$, 150 mM NaCl, pH 7.4, 4° C.) and filtering through type A/E glass fiber filters (Gelman Sciences) which have previously been placed in 0.3% (v/v) polyethyleneirnine (PEI) for 3 h. The filters are washed twice with 4 ml of PBS (4° C.), and the bound radioactivity is determined by scintillation measurement. All the assays are carried out in triplicate. The dissociation constant $K_i$ of the test substance was determined from the $IC_{50}$ of the compounds (concentration of the test substance at which 50% of the ligand bound to the receptor is displaced), the dissociation constant $K_D$ and the concentration L of [3H]-methyllycaconitine using the equation $K_1=IC_{50}/(1+L/K_D)$.

In place of [3H]-methyllycaconitine it is also possible to employ other α7 nAChR-selective radioligands such as, for example, [125I]-α-bungarotoxin or nonselective nAChR radioligands together with inhibitors of other nAChRs.

The in vitro data for the effects of the compounds of the invention show a $K_i$ of <300 nM. Representative in vitro data for the effects of the compounds of the invention are shown in Table A:

TABLE A

| Example | $K_i$ (nM) |
|---|---|
| 4 | 2.1 |
| 5 | 22.0 |
| 6 | 7.9 |
| 11 | 0.4 |
| 21 | 15.0 |
| 16 | 4.3 |
| 22 | <1.00 |

The assay described below shows that the compounds of the invention have only low affinity for 5-$HT_3$ receptors and thus act selectively on α7-nAChR.

2. Determination of the affinity of test substances for 5-$HT_3$ receptors through inhibition of [3H]GR65630 binding Membranes from HEK293 cells which express recombinant human 5-$HT_3$ receptor (RB-HS3, Receptor Biology, Inc., MD, USA) are diluted in accordance with the manufacturer's instructions in incubation buffer (50 mM tris base, pH 7.4, 5 mM $MgCl_2$, 0.5 mM EDTA, 0.1% (w/v) ascorbic acid, 10 µM pargyline and incubated in a volume of 200 µl (amount of membrane protein 3 µg) in the presence of 0.5 nM of the selective 5-$HT_3$ receptor radio ligand [3H]-GR65630 (NET 1011, Du Pont) and various concentrations of the test substance at 21° C. for 60 min. The nonspecific binding is determined by incubation in the presence of 100 µM 5-HT (5-hydroxytryptamine). The incubation is stopped by filtering through type A/E glass fiber filters (Gelman Sciences) or GF/B filters (Whatman) which have previously been placed in 0.3% (v/v) polyethyleneimine (PEI) for at least 1 h. The filters are washed three times with 3 ml of washing buffer (50 mM Tris-HCl, pH 7.4; 4° C.), and the bound radioactivity is determined by scintillation measurement. All the assays are carried out in triplicate. The dissociation constant $K_i$ of the test substance is determined from the $IC_{50}$ of the compounds (concentration of the test substance at which 50% of the ligand bound to the receptor is displaced), the dissociation constant $K_D$ and the concentration L of [3H]GR65630 ($K_i=IC_{50}/(1+L/K_D)$).

TABLE B

| Example | $K_i$ (nM) |
|---|---|
| 5 | 12000 |
| 6 | 1700 |
| 11 | 5500 |
| 21 | 1600 |
| 14 | 6900 |
| 16 | 2100 |

The suitability of the compounds of the invention for the treatment of cognitive impairments can be shown in the following animal models:

3. Object recognition test

The object recognition test is a memory test. It measures the ability of rats (and mice) to distinguish between familiar and unfamiliar objects.

The test is described by Blokland et al., NeuroReport 1998, 9, 4205-4208; A. Ennaceur at al., Behav. Brain Res. 1988, 31, 47-59; A. Ennaceur at al., Psychopharmacology 1992, 109, 321-330; and Prickaerts at al., Eur. J. Pharmacal. 1997, 337, 125-136.

In a first run, a rat is confronted in an otherwise empty observation arena of relatively large size by two identical objects. The rat will investigate, i.e. sniff round and touch, both objects extensively. In a second run, after an interval of 24 hours, the rat is put in the observation arena again. One of the familiar objects has now been replaced by a new, unfamiliar object. If a rat recognizes the familiar object, it will concentrate on investigating the unfamiliar object. However, after 24 hours, a rat has normally forgotten which object it investigated in the first run, and it will therefore inspect both objects to the same extent. Administration of a substance with a learning- and memory-improving effect may lead to a rat recognizing the object seen in the first run 24 hours previously as familiar. It will investigate the new, unfamiliar object in more detail than the familiar one. This memory ability is expressed in a discrimination index. A discrimination index of zero means that the rat investigates both objects, the old and the new, for equal times; that is to say it has not recognized the old object and reacts to both objects as if they were new. A discrimination index greater than zero means that the rat inspects the new object longer than the old one; that is to say the rat has recognized the old object.

4. Social recognition test:

The social recognition test is a test to examine the learning- or memory-improving effect of test substances.

Adult rats housed in groups are placed singly in test cages 30 minutes before the start of the test. Four minutes before the start of the test, the test animal is put in an observation box. After this adaptation time, a juvenile animal is put in with the test animal and the time for which the adult animal investigates the juvenile animal is measured for 2 minutes (trial 1). All behaviors clearly directed at the young animal are measured, i.e. anogenital inspection, pursuit and grooming, during which the old animal is no further than 1 cm from the young animal. The juvenile animal is then taken out, and the adult is left in its test cage (for 24-hour retention, the animal is returned to its home cage). The adult test animal is treated with test substance before or after the first test. Depending on the timing of the treatment, the learning or the storage of the information about the young animal can be influenced by the substance. After a fixed period (retention), the test is repeated (trial 2). A larger difference between the investigation times measured in trials 1 and 2 means that the adult animal has remembered the young animal better.

The novel active ingredients can be converted in a known manner into conventional formulations such as tablets, coated tablets, pills, granules, aerosols, syrups, emulsions, suspensions and solutions, using inert, nontoxic, pharmaceutically suitable carriers or solvents. In these cases, the therapeutically active compound should in each case be present in a concentration of about 0.5 to 90% by weight of the formulation, i.e. in amounts which are sufficient to reach the stated dose range.

The formulations are produced for example by extending the active ingredients with solvents and/or carriers, where appropriate with use of emulsifiers and/or dispersants, it being possible for example when water is used as diluent where appropriate to use organic solvents as auxiliary solvents.

Administration takes place in a conventional way, preferably orally, transdermally or parenterally, especially perlingually or intravenously. However, it can also take place by inhalation through the mouth or nose, for example with the aid of a spray, or topically via the skin.

It has generally proved advantageous to administer amounts of about 0.001 to 10 mg/kg, on oral administration preferably about 0.005 to 3 mg/kg, of body weight to achieve effective results.

It may, nevertheless, be necessary where appropriate to deviate from the stated amounts, in particular as a function of the body weight or of the mode of administration, of the individual behavior toward the medicament, the nature of its formulation and the time or interval over which administration takes place. Thus, it may be sufficient in some cases to make do with less than the aforementioned minimum amount, whereas in other cases the stated upper limit must be exceeded. Where larger amounts are administered, it may be advisable to divide these into a plurality of single doses over the day.

Unless indicated otherwise, all quantitative data relate to percentages by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

ABBREVIATIONS

BINAP 2,2'-Bis-(diphenylphosphino)-1,1'-binaphthyl
DAD Diode array detector
DMF N,N-Dimethylformamide
DMSO Dimethyl sulfoxide
EDTA Ethylenediaminetetraacetic acid
eq. Equivalent
ESI Electrospray ionization (in MS)
HATU O-(7-Azabenzotriazol-1-yl)-N,N,N',N'-tetramethyluronium hexafluorophosphate
HOBt 1-Hydroxy-1H-benzotriazole×$H_2O$
HPLC High pressure/high performance liquid chromatography
LC-MS Coupled liquid chromatography-mass spectroscopy
MS Mass spectroscopy
NMR Nuclear magnetic resonance spectroscopy
PBS Phosphate buffered saline
$Pd_2(dba)_3$ Tris(dibenzylideneacetone)dipalladium(0)
RT Room temperature (20° C.)
$R_t$ Retention time (in HPLC)
TBTU O-(Benzotriazol-1-yl)-N,N,N',N'-tetramethyluronium tetrafluoroborate
THF Tetrahydrofuran
Tris Tris-(hydroxymethyl)-aminomethane HPLC Method:

Instrument: HP 1100 with DAD detection; column: Kromasil RP-18, 60 mm×2 mm, 3.5 µm; Eluent: A=5 ml of $HClO_4$/L of $H_2O$, B=acetonitrile; gradient: 0 min 2% B, 0.5 min 2% B, 4.5 min 90% B, 6.5 min 90% B; flow rate: 0.75 ml/min; Temp.: 30° C.; detection: UV 210 nm.

LC-MS Method:

Instrument: Micromass Platform LCZ, HP1100; column; Symmetry C18, 50 mm×2.1 mm, 3.5 µm; Eluent A: water+ 0.05% formic acid, Eluent B: acetonitrile+0.05% formic acid; gradient: 0.0 min 90% A→4.0 min 10% A→6.0 min 10% A; oven: 40° C.; flow rate: 0.5 ml/min; UV detection: 208-400 nm.

General Method A

Synthesis of 1-benzothiophene-2-carboxylic acids

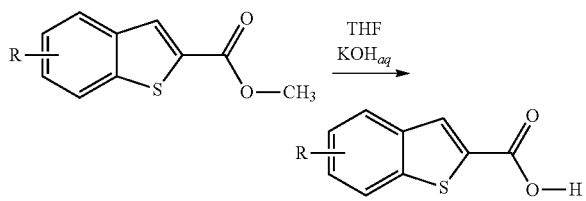

The appropriate methyl 1-benzothiophene-2-carboxylate is mixed with a mixture of equal parts of THF and 2 N aqueous potassium hydroxide solution (0.28-0.47 M solution). The reaction mixture is left to stir at room temperature overnight. The THF is removed under reduced pressure, and the aqueous reaction mixture is acidified with concentrated hydrochloric acid. The resulting precipitate is filtered off with suction and dried in vacuo at 40° C.

General Method B

Amide linkage between 3-quinuclidinamine and 2-benzothiophenecarboxylic acids 1.0 eq. of the appropriate enantiomeric 3-quinuclidinamine hydrochloride, 1.0 eq. of the carboxylic acid and 1.2 eq. of HATU in DMF at 0° C. are stirred after addition of 1.2 eq. of N,N-diisopropylethylamine for 30 min. Then a further 2.4 eq. of N,N-diisopropylethylamine are added, and the mixture is stirred at RT overnight.

Starting Compounds

Example 1A

Methyl 7-bromo-1-benzothiophene-2-carboxylate

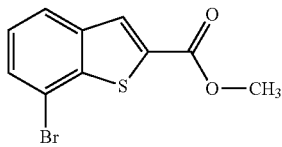

Under an argon atmosphere, 8.2 g (205.7 mmol) of sodium hydride (60% in liquid paraffin) are introduced into 300 ml of absolute DMSO. At room temperature, 16.0 g (150.9 mmol) of methyl mercaptoacetate are slowly added dropwise to the reaction mixture, which is stirred at room temperature until hydrogen evolution ceases (about 15 min). A solution of 27.8 g (137.1 mmol) of 3-bromo-2-fluorobenzaldehyde in 50 ml of absolute DMSO is added at room temperature to the reaction mixture. The latter is stirred until the reaction is complete and then poured into ice-water. The resulting precipitate is filtered off with suction and dried in vacuo at 40° C. overnight. 20.57 g of a mixture of the title compound and of the corresponding acid (approx. 1:1) are obtained.

Example 2A

Methyl 6-bromo-1-benzothiophene-2-carboxylate

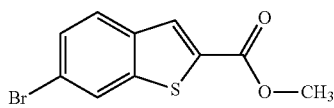

Under an argon atmosphere, 1.93 g (48.3 mmol) of sodium hydride (60% in liquid paraffin) are introduced into 60 ml of absolute DMSO. At room temperature, 3.76 g (35.5 mmol) of methyl mercaptoacetate are slowly added dropwise to the reaction mixture, which is stirred at room temperature until hydrogen evolution ceases (about 15 min). A solution of 6.54 g (32.2 mmol) of 4-bromo-2-fluorobenzaldehyde and 15 ml of absolute DMSO are added at room temperature to the reaction mixture. The latter is stirred until the reaction is complete and then poured into ice-water. The resulting precipitate is filtered off with suction and dried in vacuo at 40° C. overnight. 4.06 g (46.4% of theory) of the title compound are obtained.

$^1$H-NMR (200.1 MHz, DMSO-$d_6$): δ=8.42 (d, 1H), 8.22 (s, 1H), 7.98 (d, 1H), 7.65 (dd, 1H), 3.90 (s, 3H)

HPLC: $R_t$=5.3 min

MS (ESIpos): m/z=270 (M$^+$), 288 (M+NH$_4$)$^+$, 305 (M+N$_2$H$_7$)$^+$

Example 3A

Methyl 6-nitro-1-benzothiophene-2-carboxylate

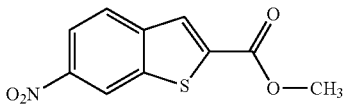 [SMILES: COC(=O)c1cc2ccc([N+](=O)[O-])cc2s1]

2 g (10.2 mmol) of 2,4-dinitrobenzaldehyde, 1.08 g (10.2 mmol) of methyl mercaptoacetate and 2.84 ml (20.4 mmol) of triethylamine are successively dissolved in 6 ml of DMSO. The reaction solution is heated at 80° C. for 1 h and then poured into 200 ml of ice-water. Several dichloromethane extractions are carried out. The combined organic phases are dried over sodium sulfate and concentrated in vacuo. Chromatography (mobile phase: dichloromethane) on silica gel affords 1.12 g (46.1% of theory) of the title compound.

$^1$H-NMR (300 MHz, CDCl$_3$): δ=8.80 (d, 1H), 8.27 (dd, 1H), 8.13 (s, 1H), 8.00 (d, 1H), 3.99 (s, 3H)

HPLC: $R_t$=4.7 min

MS (ESIpos): m/z=255 (M+NH$_4$)$^+$

Example 4A

6-Bromo-1-benzothiophene-2-carboxylic acid

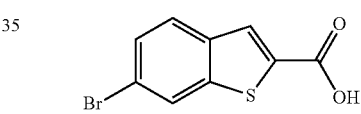

3.55 g (93.5% of theory) of the desired product are obtained from 4.0 g (14.8 mmol) of methyl 6-bromo-1-benzothiophene-2-carboxylate by general method A.

$^1$H-NMR (400.1 MHz, DMSO-$d_6$); δ=13.48 (s, 1H, br), 8.38 (s, 1H), 8.22 (s, 1H), 7.96 (d, 1H), 7.63 (m, 1H)

HPLC: $R_t$=4.5 min.

Example 5A

7-Bromo-1-benzothiophene-2-carboxylic acid

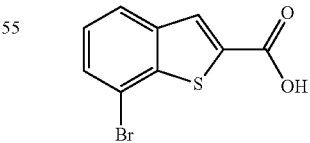

8.99 g (91.0% of theory) of the desired product are obtained from 10.0 g (36.9 mmol) of methyl 7-bromo-1-benzothiophene-2-carboxylate by general method A.

$^1$H-NMR (200.1 MHz, DMSO-$d_6$): δ=13.76 (s, 1H, br), 8.28 (s, 1H), 8.07 (d, 1H), 7.78 (d, 1H), 7.46 (dd, 1H)

HPLC: 99.1%, $R_t$=4.4 min.

Example 6A

6-Nitro-1-benzothiophene-2-carboxylic acid

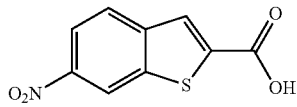

1.20 g (91.4% of theory) of the desired product are obtained from 1.4 g (5.90 mmol) of methyl 6-nitro-1-benzothiophene-2-carboxylate by general method A.

$^1$H-NMR (200.1 MHz, DMSO-$d_6$): δ=8.91 (d, 1H), 8.14 (dd, 1H), 8.02 (d, 1H), 7.69 (s, 1H)

HPLC: $R_t$=4.1 min.

MS (ESIpos): m/z=241 (M+NH$_4$)$^+$

Example 7A

6-[(tert-Butoxycarbonyl)amino]-1-benzothiophene-2-carboxylic acid

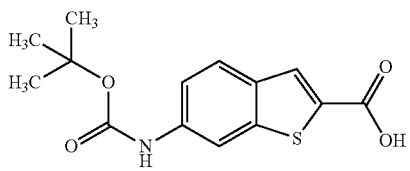 [SMILES: CC(C)(C)OC(=O)Nc1ccc2cc(C(=O)O)sc2c1]

400 mg (2.07 mmol) of 6-amino-1-benzothiophene-2-carboxylic acid and 1.36 g (6.21 mmol) of di-tert-butyl pyrocarbonate are stirred in a mixture of 5 ml of dioxane and 10 ml of aqueous 1 N sodium bicarbonate solution at room temperature for 18 h. The solution is adjusted to pH 5-6 with 10% strength aqueous citric acid solution and extracted four times with ethyl acetate. The combined organic phases are dried over sodium sulfate and concentrated. The residue is chromatographed on silica gel (mobile phase: dichloromethane/methanol). 214 mg (30% of theory) of the title compound are obtained.

MS (ESIpos): m/z=316 (M+Na)$^+$

Example 8A

N-[(3M-1-Azabicyclo[2.2.2]oct-3-yl]-7-bromo-1-benzothiophene-2-carboxamide hydrochloride

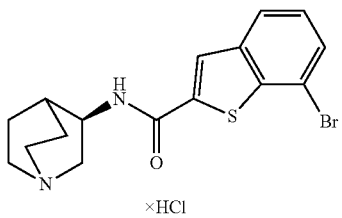 [SMILES: O=C(N[C@H]1CN2CCC1CC2)c1cc2cccc(Br)c2s1]

903.8 mg (3.52 mmol) of 7-bromo-1-benzothiophene-2-carboxylic acid, 700.0 mg (3.52 mmol) of R-aminoquinulidine dihydrochloride, 1604.0 mg (4.22 mmol) of HATU, 1635.7 mg (12.66 mmol) of N,N-diisopropylethylamine and 7.0 ml of DMP are reacted by general method B. The reaction mixture is purified by preparative HPLC. The product is dissolved in a 1:1 mixture of 4 M HCl in dioxane and 1 N hydrochloric acid and then concentrated and dried under high vacuum. 1087 mg (77% of theory) of the title compound are obtained.

$^1$H-NMR (200.1 MHz, DMSO-$d_6$): δ=10.01 (s, 1H, br), 9.15 (d, 1H), 8.47 (s, 1H), 8.02 (m, 1H), 7.74 (m, 1H), 7.43 (dd, 1H), 4.34 (m, 1H), 3.80-3.10 (m, 6H), 2.22 (m, 1H), 2.14 (m, 1H), 1.93 (m, 2H), 1.78 (m, 1H)

HPLC: $R_t$=4.1 min

MS (ESIpos): m/z=367 (M+H, $^{81}$Br)$^+$, 365 (M+H, $^{79}$Br)$^+$

Example 9A

N-[(3R)-1-Azabicyclo[2.2.2]oct-3-yl]-6-bromo-1-benzothiophene-2-carboxamide hydrochloride

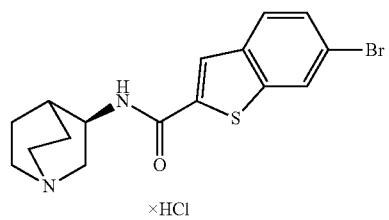 [SMILES: O=C(N[C@H]1CN2CCC1CC2)c1cc2ccc(Br)cc2s1]

900.0 mg (3.50 mmol) of 4-bromo-1-benzodaiophene-2-carboxylic acid, 697.0 mg (3.50 mmol) of R-aminoquinuclidine dihydrochloride, 1597.1 mg (4.20 mmol) of HATU, 1628.7 mg (12.60 mmol) of N,N-diisopropylethylamine and 8.0 ml of DMF are reacted by general method B. The reaction mixture is purified by preparative HPLC. The product is dissolved in a 1:1 mixture of 4 M HCl in dioxane and 1 N hydrochloric acid and then concentrated. Recrystallization from methanol/ethanol (1:10) yields 594 mg (42.1% of theory) of the title compound.

$^1$H-NMR (300.1 MHz, DMSO-$d_6$): δ=9.81 (s, 1H, br), 8.76 (m, 1H), 8.33 (s, 1H), 8.22 (s, 1H), 7.91 (d, 1H), 7.59 (dd, 1H), 4.15 (m, 1H), 3.51-2.93 (m, 6H), 2.12-1.92 (m, 2H), 1.79 (m, 2H), 1.58 (m, 1H)

HPLC: $R_t$=4.1 min

MS (ESIpos): m/z 366 (M, $^{81}$Br), 364 (M, $^{79}$Br)$^+$

Example 10A

N-[(3R)-1-Azabicyclo[2.2.2]oct-3-yl]-6-nitro-1-benzothiophene-2-carboxamide hydrochloride

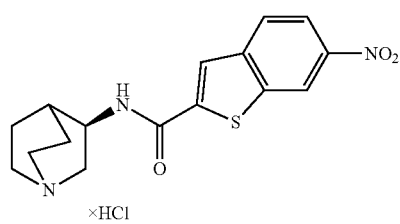 [SMILES: O=C(N[C@H]1CN2CCC1CC2)c1cc2ccc([N+](=O)[O-])cc2s1]

290.0 nag (1.30 mmol) of 6-nitro-1-benzothiophene-2-carboxylic acid, 258.7 mg (1.30 mmol) of R-aminoquinuclidine dihydrochloride, 592.8 mg (1.56 mmol) of HATU, 604.5 mg (4.68 mmol) of N,N-diisopropylethylamine and 2.0 ml of DMF are reacted by general method B. The reaction mixture is purified by preparative HPLC, mixed with 1 N hydrochloric acid and then concentrated. Recrystallization from isopropanol yields 297 mg (62.1% of theory) of the title compound.

$^1$H-NMR (400 MHz, MeOD-d$_4$): δ=8.95 (s, 1H), 8.28 (dd, 1H), 8.20 (s, 1H), 811 (d, 1H), 4.46 (m, 1H), 3.87 (m, 1H), 3.52-3.22 (m, 5H), 2.40 (m, 1H), 2.28 (m, 1H), 2.11 (m, 1H)

HPLC: R$_t$=3.8 min.

MS (ESIpos): m/z=332 (M+H)$^+$.

Example 11A

N-[(3R)-1-Azabicyclo[2.2.2]oct-3-yl]-7-amino-1-benzothiophene-2-carboxamide dihydrochloride

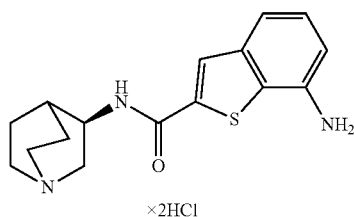 [SMILES: Nc1cccc2cc(C(=O)N[C@H]3CN4CCC3CC4)sc12]

87 mg (0.22 mmol) of N-[(3R)-1-Azabicyclo[2.2.2]oct-3-yl]-3-bromo-1-benzothiophene-2-carboxamide hydrochloride, 47.1 mg (0.26 mmol) of benzophenone imine, 12.1 mg (0.02 mmol) of rac-BINAP, 45.8 mg (0.48 mmol) of sodium tert-butoxide and 6.0 mg (0.01 mmol) of Pd$_2$(dba)$_3$ are put under argon in a heat-dried flask. 1.5 ml of toluene are added, and the reaction mixture is heated to 80° C. After 30 min, 0.5 ml of THF, and after 6 h a further 6.0 mg (0.01 mmol) of Pd$_2$(dba)$_3$, are added. After a further 6 h, a filtration (0.45 μm filter) is followed by purification by preparative HPLC. The resulting benzophenone imine adduct is dissolved in a 1:1 mixture of THF and methanol with the addition of 20% by volume 1 N hydrochloric acid. After 1 h at room temperature, the reaction mixture is concentrated. The resulting solid is stirred with acetonitrile and filtered. Drying under high vacuum results in 17 mg (21% of theory) of the title compound.

$^1$H-NMR (400.1 MHz, D$_2$O): δ=8.11 (s, 1H), 7.89 (d, 1H), 7.53 (dd, 1H), 7.37 (d, 1H), 4.48 (m, 1H), 3.87 (m, 1H), 3.52-3.30 (m, 5H), 2.44 (m, 1H), 2.27 (m, 1H), 2.12 (m, 2H), 2.00 (m, 1H)

HPLC: R$_t$=2.9 min

MS (ESIpos): m/z=302 (M+H)$^+$

Example 12A

6-Amino-N-[(3R)-1-azabicyclo[2.2.2]oct-3-yl]-1-benzothiophene-2-carboxamide dihydrochloride

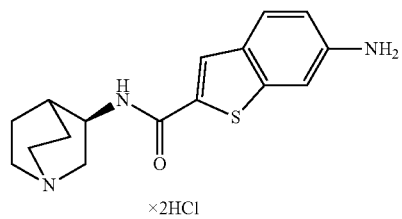 [SMILES: Nc1ccc2cc(C(=O)N[C@H]3CN4CCC3CC4)sc2c1]

Method A):

15 mg (0.05 mmol) of 6-[(tert-butoxycarbonyl)amino]-1-benzothiophene-2-carboxylic acid, 10.2 mg (0.05 mmol) of R-aminoquinuclidine dihydrochloride, 21.4 mg (0.06 mmol) of HATU, 21.8 mg (0.17 mmol) of N,N-diisopropylethylamine and 1 ml of DMF are reacted by general method B. The reaction mixture is purified by preparative HPLC. The product is mixed with 5 ml of 4 M HCl in dioxane and stirred at room temperature for 30 min. A mixture is concentrated and dried under high vacuum. 17 mg (98% of theory) of the title compound are obtained.

Method B):

247 mg (0.67 mmol) of N-[(3R)-1-azabicyclo[2.2.2]oct-3-yl]-6-nitro-1-benzothiophene-2-carboxamide hydrochloride are suspended in 1.6 ml of 1 N hydrochloric acid and 4.3 ml of methanol and, under argon, 25.6 mg of palladium on carbon (5%) are added. The mixture is stirred under a hydrogen atmosphere (atmospheric pressure) for 2 h. The contents of the flask are filtered through kieselguhr and evaporated to dryness in vacuo. 241 mg (95.6% of theory) of the title compound are obtained.

Method C):

10 ml of a 1:1 mixture of THF and toluene are added to a mixture of 730 mg (1.76 mmol) of N-[(3R)-1-azabicyclo[2.2.2]oct-3-yl]-6-bromo-1-benzothiophene-2-carboxamide hydrochloride, 638.9 mg (3.53 mmol) of benzophenone imine, 109.8 mg (0.18 mmol) of rac-BINAP, 508.2 mg (5.29 mmol) of sodium tert-butoxide and 161.4 mg (0.18 mmol) of Pd$_2$(dba)$_3$, and the reaction mixture is heated at 85° C. overnight. The contents of the flask are concentrated to about 7 ml and purified by preparative HPLC. The resulting benzophenone imine adduct is dissolved in a mixture of 5 ml of methanol and 3 ml of 1 N hydrochloric acid and stirred at room temperature for 1 h. Concentration of the solution is followed by recrystallization from methanol/diethyl ether and further purification by preparative HPLC. The product fractions are mixed with 1 N of hydrochloric acid. Concentration and drying under high vacuum result in 67 mg (10.1% of theory) of the title compound.

$^1$H-NMR (400.1 MHz, D$_2$O): δ=7.95 (m, 2H), 7.88 (m, 1H), 7.32 (m, 1H), 4.37 (m, 1H), 3.80-3.69 (m, 2H), 3.40-3.18 (m, 4H), 2.32 (m, 1H), 2.16 (m, 1H), 2.00 (m, 2H), 1.89 (m, 1H)

HPLC: R$_t$=2.7 min

MS (ESIpos): m/z=302 (M+H)$^+$

Example 13A 2-(Hydroxymethyl)-5-nitrophenol

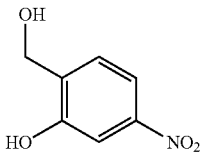

10.0 g (54.6 mmol) of 4-nitrosalicylic acid are introduced into 100 ml of THF. While cooling in ice, 109 ml of 1 M borane-THF complex are added, and the mixture is stirred at room temperature overnight. It is concentrated and the precipitate is filtered off with suction. The solid is dissolved in ethyl acetate and dried over magnesium sulfate. After concentration and drying under high vacuum, the tide compound is immediately reacted further.

LC-MS (ESIpos): m/z=169 (M+)

Example 14A

2-Hydroxy-4-nitrobenzaldehyde

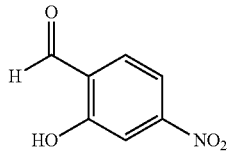

6.0 g (35.5 mmol) of 2-(hydroxymethyl)-5-nitrophenol and 3.1 g (35.5 mmol) of activated manganese(IV) oxide in 100 ml of chloroform are heated under reflux for 20 h. The mixture is filtered through kieselguhr, concentrated and dried under high vacuum. The title compound is immediately reacted further.

MS (ESIpos): m/z=167 (M+)

Example 15A

6-Nitro-1-benzofuran-2-carboxylic acid

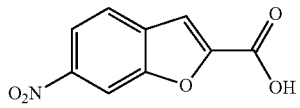

5.8 g (34.7 mmol) of 2-hydroxy-4-nitrobenzaldehyde, 1.28 g (3.5 mmol) of tetrabutylammonium iodide and 19.2 g (138.8 mmol) of potassium carbonate are mixed, 7.9 g (72.9 mmol) of methyl chloroacetate are added, and the mixture is heated at 130° C. for 12 h. 100 ml of THF are added and, while cooling in ice, 11.7 g (208.2 mmol) of potassium hydroxide are added. Addition of 100 ml of water is followed by stirring at room temperature for 20 h. The pH is adjusted to pH 1 with conc. hydrochloric acid. The mixture is extracted with ethyl acetate. The organic phase is washed with water and dried over sodium sulfate. Addition of silica gel is followed by concentration and chromatography on silica gel (mobile phase: toluene/methanol/acetic acid). Concentration of the product fractions and drying in vacuo result in 1.31 g (18.2% of theory) of the title compound.

HPLC: R$_t$=3.8 min

MS (ESIpos): m/z=225 (M+NH$_4$)$^+$

Example 16A

N-[(3R)-1-Azabicyclo[2.2.2]oct-3-yl]-6-nitro-1-benzofuran-2-carboxamide

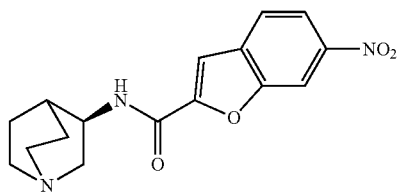 [SMILES: O=C(N[C@H]1CN2CCC1CC2)c1cc2ccc([N+](=O)[O-])cc2o1]

1.3 g (5.02 mmol) of 6-nitro-1-benzofuran-2-carboxylic acid, 1.0 g (5.02 mmol) of R-aminoquinuclidine dihydrochloride, 2.29 g (6.02 mmol) of HATU, 2.34 g (18.07 mmol) of N,N-diisopropylethylamine and 10 ml of DMF are reacted by general method B. The mixture is concentrated in vacuo and extracted with 1 N sodium hydroxide solution and with ethyl acetate, the organic phase is dried over sodium sulfate and concentrated, and the residue is dissolved in methanol. Dowex 50WX2-200 ion exchanger resin is added, and within 1 h, the mixture is concentrated in a rotary evaporator. The resin is washed successively with methanol, DMF, methanol, THF, methanol, dichloromethane, methanol and 10% triethylamine in methanol. The product fraction is concentrated 1.75 g (99% of theory) of the title compound are obtained.

HPLC: R$_t$=3.6 min.

MS (ESIpos): m/z=316 (M+H)$^+$

Example 17A

6-Amino-N-[(3R)-1-azabicyclo[2.2.2]oct-3-yl]-1-benzofuran-2-carboxamide

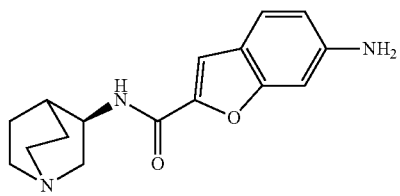 [SMILES: Nc1ccc2cc(C(=O)N[C@H]3CN4CCC3CC4)oc2c1]

1.55 g (4.92 mmol) of N-[(3R)-1-azabicyclo[2.2.2]oct-3-yl]-6-nitro-1-benzofuran-2-carboxamide are dissolved in 15 ml of 2 M tin(II) chloride solution in DMF and stirred at room temperature overnight. Dowex 50WX2-200 ion exchanger resin is added and, within 1 h, the mixture is concentrated in a rotary evaporator. The resin is washed successively with water, DMF, methanol, dichloromethane, methanol and 10% triethylamine in methanol. The product fraction is concentrated and chromatographed on silica gel (mobile phase: dichloromethane/methanol/triethylamine).

Concentration in vacuo results in 642.8 mg (45.8% of theory) of the title compound.

HPLC: $R_t$=2.6 min.
MS (ESIpos): m/z=286 (M+H)$^+$.

Exemplary Embodiments

Example 1

6-[(Anilinocarbonyl)amino]-N-[(3R)-1-azabicyclo[2.2.2]oct-3-yl]-1-benzothiophene-2-carboxamide hydrochloride

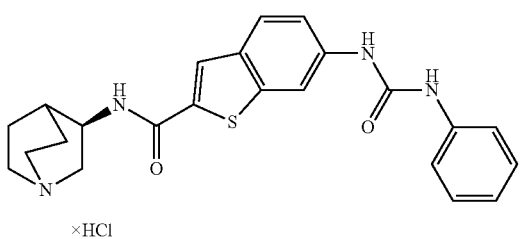 [SMILES: O=C(Nc1ccccc1)Nc1ccc2cc(C(=O)N[C@H]3CN4CCC3CC4)sc2c1]

A solution of 80 mg (0.21 mmol) of 6-amino-N-[(3R)-1-azabicyclo[2.4.2]-3-yl]-1-benzothiophene-2-carboxamide dihydrochloride in 4 ml of THF is mixed with 59.6 µl (0.43 mmol) of triethylamine and 50.9 mg (0.43 mmol) of phenyl isocyanate. After 16 h at room temperature, the reaction mixture is purified by preparative HPLC. The concentrated product fraction is dissolved in a mixture of acetonitrile and 1 N hydrochloric acid (5:1), again concentrated and dried under high vacuum. 35 mg (35.8% of theory) of the title compound are obtained.

$^1$H-NMR (400 MHz, Methanol-d$_4$): δ=8.21 (s, 1H), 8.00 (s, 1H), 7.82 (d, 1H), 7.45 (m, 2H), 7.38 (dd, 1H), 7.30 (m, 2H), 7.03 (dd, 1H), 4.43 (m, 1H), 3.85 (m, 1H), 3.52-3.20 (m, 5H), 2.39 (m, 1H), 2.28 (m, 1H), 2.10 (m, 2H), 1.96 (m, 1H)

HPLC: $R_t$=3.9 min.
MS (ESIpos): m/z=421 (M+H)$^+$ (free base).

Example 2

N-[(3R)-1-Azabicyclo[2.2.2]oct-3-yl]-6-({[(4-chlorophenyl)amino]carbonyl}amino)-1-benzothiophene-2-carboxamide hydrochloride

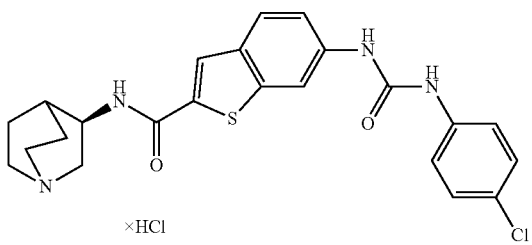 [SMILES: O=C(Nc1ccc(Cl)cc1)Nc1ccc2cc(C(=O)N[C@H]3CN4CCC3CC4)sc2c1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 µl (0.21 mmol) of triethylamine and 32.8 mg (0.21 mmol) of 4-chlorophenyl isocyanate. After 16 h at room temperature, the mixture is concentrated in vacuo. The residue is dissolved in a 1:1 mixture of water and acetonitrile and purified by preparative HPLC. The concentrated product fraction is dissolved in a mixture of acetonitrile and 1 N hydrochloric acid (5:1), again concentrated and dried under high vacuum. 29 mg (55.2% of theory) of the title compound are obtained.

$^1$H-NMR (400 MHz, Methanol-d$_4$): δ=8.21 (s, 1H), 8.02 (s, 1H), 7.82 (d, 1H), 7.47 (m, 2H), 7.38 (dd, 1H), 7.29 (m, 2H), 4.44 (m, 1H), 3.85 (m, 1H), 3.52-3.12 (m, 5H), 2.39 (m, 1H), 2.28 (m, 1H), 2.10 (m, 2H), 1.96 (m, 1H)

HPLC: $R_t$=4.1 min.
MS (ESIpos): m/z=455 (M+H)$^+$ (free base).

Example 3

N-[(3R)-1-Azabicyclo[2.2.2]oct-3-yl]-6-({[(2-triethoxyphenyl)amino]carbonyl}-amino)-1-benzothiophene-2-carboxamide hydrochloride

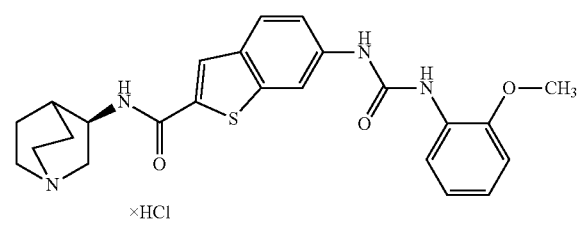 [SMILES: COc1ccccc1NC(=O)Nc1ccc2cc(C(=O)N[C@H]3CN4CCC3CC4)sc2c1]

A solution of 80 mg (0.21 mmol) of 6-amino-N-[(3R)-1-azabicyclo[2.2.2]oct-3-yl]-1-benzothiophene-2-carboxamide dihydrochloride in 4 ml of THF is mixed with 596 µl (0.43 mmol) of triethylamine and 63.8 mg (0.43 mmol) of 2-methoxyphenyl isocyanate. After 16 h at room temperature, the product is purified by preparative HPLC. The concentrated product fraction is dissolved in a mixture of acetonitrile and 1 N hydrochloric acid (5:1), again concentrated and dried under high vacuum. 10 mg (9.6% of theory) of the title compound are obtained.

$^1$H-NMR (400 MHz, Methanol-d$_4$): δ=8.23 (s, 1H), 8.09 (d, 1H), 8.03 (s, 1H), 7.82 (d, 1H), 7.36 (m, 1H), 7.00 (m, 2H), 6.92 (m, 1H), 4.44 (m, 1H), 3.93 (s, 3H), 3.84 (m, 1H), 3.48 (m, 1H), 3.42-3.25 (m, 4H), 2.39 (m, 1H), 2.28 (m, 1H), 2.10 (m, 2H), 1.96 (m, 1H)

HPLC: $R_t$=4.0 min.
MS (ESIpos): m/z=451 (M+H)$^+$ (free base).

Example 4

N-[(3R)-1-Azabicyclo[2.2.2]oct-3-yl]-6-({[(4-methoxyphenyl)amino]carbonyl}-amino)-1-benzothiophene-2-carboxamide hydrochloride

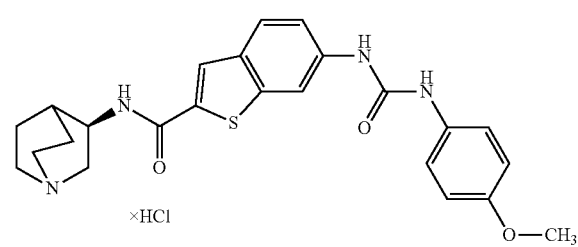 [SMILES: COc1ccc(NC(=O)Nc2ccc3cc(C(=O)N[C@H]4CN5CCC4CC5)sc3c2)cc1]

A solution of 80 mg (0.21 mmol) of 6-amino-N-[(3R)-1-azabicyclo[2.2.2]oct-3-yl]-1-benzothiophene-2-carboxamide dihydrochloride in 4 ml of THF is mixed with 59.6 µl (0.43 mmol) of triethylamine and 63.8 mg (0.43 mmol) of 4-methoxyphenyl isocyanate. After 16 h at room temperature, the product is purified by preparative HPLC. The concentrated product fraction is dissolved in a mixture of acetonitrile and 1 N hydrochloric acid (5:1), again concentrated and dried under high vacuum. 55 mg (52.8% of theory) of the title compound are obtained.

$^1$H-NMR (400 MHz, Methanol-$d_4$): δ=8.20 (s, 1H), 8.00 (s, 1H), 7.81 (d, 1H), 7.35 (m, 3H), 6.89 (m, 2H), 4.44 (m, 1H), 3.85 (m, 1H), 3.78 (s, 3H), 3.52-3.22 (m, 5H), 2.39 (m, 1H), 2.28 (m, 1H), 2.10 (m, 2H), 1.96 (m, 1H)

HPLC: $R_t$=3.8 min.

MS (ESIpos): m/z=451 (M+H)$^+$ (free base).

Example 5

N-[(3R)-1-Azabicyclo[2.2.2]oct-3-yl]-6-({[(2-phenylethyl)amino]carbonyl}amino)-1-benzothiophene-2-carboxamide hydrochloride

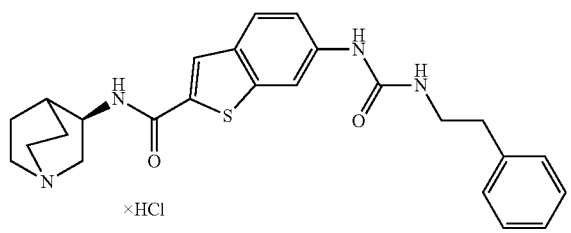 [SMILES: O=C(NCCc1ccccc1)Nc1ccc2cc(C(=O)N[C@H]3CN4CCC3CC4)sc2c1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 µl (0.21 mmol) of triethylamine and 31.5 mg (0.21 mmol) of (2-isocyanatoethyl)benzene. After 18 h at room temperature, the product is purified by preparative HPLC. The concentrated product fraction is dissolved in a mixture of acetonitrile and 1 N hydrochloric acid (5:1), again concentrated and dried under high vacuum. 32 mg (61.8% of theory) of the title compound are obtained.

$^1$H-NMR (400 MHz, Methanol-$d_4$): δ=8.11 (s, 1H), 8.02 (s, 1H), 7.77 (d, 1H), 7.36-716 (m, 6H), 4.44 (m, 1H), 3.83 (m, 1H), 3.55-3.23 (m, 7H), 2.86 (tr, 2H), 2.38 (m, 1H), 2.28 (m, 1H), 2.10 (m, 2H), 1.96 (m, 1H)

HPLC: $R_t$=4.0 min.

MS (ESIpos): m/z=449 (M+H)$^+$ (free base).

Example 6

N-[(3R)-1-Azabicyclo[2.2.2]oct-3-yl]-6-({[(3-cyanophenyl)amino]carbonyl}amino)-1-benzothiophene-2-carboxamide hydrochloride

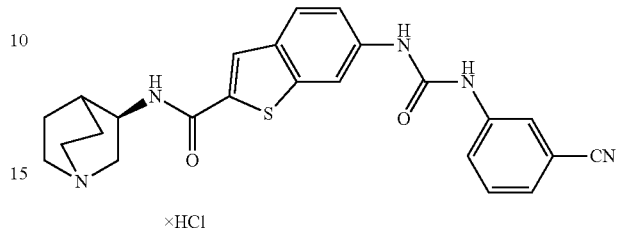

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 µl (0.21 mmol) of triethylamine and 30.8 mg (0.21 mmol) of 3-cyanophenyl, isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 32 mg (62.1% of theory) of the title compound are obtained.

$^1$H-NMR (400 MHz, Methanol-$d_4$): δ=8.23 (s, 1H), 8.00 (m, 2H), 7.83 (d, 1H), 7.67 (d, 1H), 7.47 (dd, 1H), 7.39 (m, 2H), 4.43 (m, 1H), 3.86 (m, 1H), 3.53-3.18 (m, 5H), 2.39 (m, 1H), 2.28 (m, 1H), 2.10 (m, 2H), 1.97 (m, 1H).

HPLC: $R_t$=3.9 min.

MS (ESIpos): m/z=446 (M+H)$^+$ (free base).

Example 7

N-[(3R)-1-Azabicyclo[2.2.2]oct-3-yl]-6-({[(3-bromophenyl)amino]carbonyl}amino)-1-benzothiophene-2-carboxamide hydrochloride

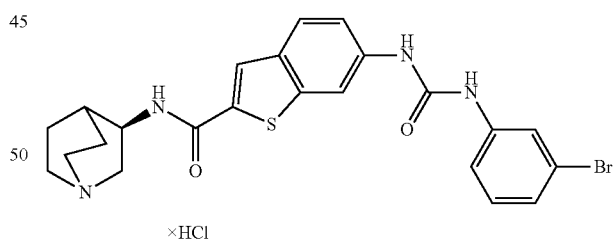

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 µl (0.21 mmol) of triethylamine and 42.3 mg (0.21 mmol) of 3-bromophenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 43 mg (75.1% of theory) of the title compound are obtained.

$^1$H-NMR (400 MHz, Methanol-$d_4$): δ=8.21 (s, 1H), 8.02 (m, 1H), 7.82 (m, 2H), 7.37 (m, 2H), 7.19 (m, 2H), 4.45 (m, 1H), 3.84 (m, 1H), 3.54-3.20 (m, 5H), 2.39 (m, 1H), 2.28 (m, 1H), 2.11 (m, 2H), 1.97 (m, 1H)

HPLC: $R_t$=4.2 min.

MS (ESIpos): m/z=499 (M+H)$^+$ (free base).

Example 8

N-[(3R)-1-Azabicyclo[2.2.2]oct-3-yl]-6-({[(2-ethoxyphenyl)amino]carbonyl}amino)-1-benzothiophene-2-carboxamide hydrochloride

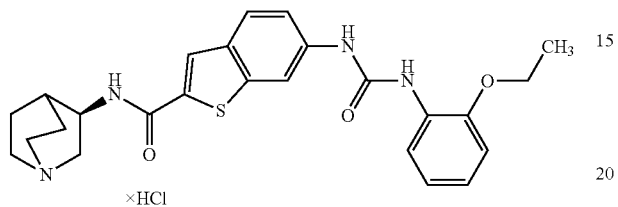

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 34.9 mg (0.21 mmol) of 2-ethoxyphenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 10 mg (18.7% of theory) of the title compound are obtained.

$^1$H-NMR (400 MHz, Methanol-$d_4$): δ=8.25 (s, 1H), 8.09 (d, 1H), 8.00 (s, 1H), 7.82 (d, 1H), 7.38 (d, 1H), 6.98 (m, 2H), 6.91 (m, 1H), 4.43 (m, 1H), 4.16 (q, 2H), 3.86 (m, 1H), 3.53-3.21 (m, 5H), 2.39 (m, 1H), 2.28 (m, 1H), 2.10 (m, 2H), 1.97 (m, 1H), 1.50 (tr, 3H)

HPLC: $R_t$=4.2 min.

MS (ESIpos): m/z=465 (M+H)$^+$ (free base).

Example 9

N-[(3R)-1-Azabicyclo[2.2.2]oct-3-yl]-6-({[(4-(dimethylamino)phenyl)amino]-carbonyl}amino)-1-benzothiophene-2-carboxamide hydrochloride

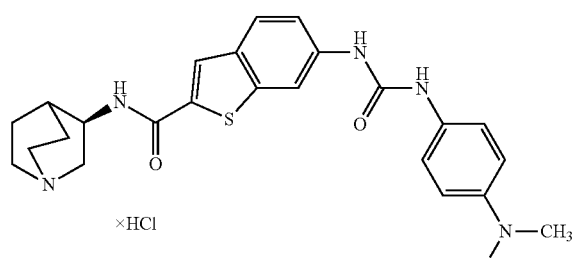

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 34.7 mg (0.21 mmol) of 4-N,N-dimethylaminophenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 21 mg (38.7% of theory) of the title compound are obtained.

$^1$H-NMR (400 MHz, Methanol-$d_4$): δ=8.24 (s, 1H), 8.05 (s, 1H), 7.84 (d, 1H), 7.72 (m, 2H), 7.58 (m, 2H), 7.39 (d, 1H), 4.45 (m, 1H), 3.84 (m, 1H), 3.53-3.20 (m, 11H), 2.39 (m, 1H), 2.28 (m, 1H), 2.11 (m, 2H), 1.97 (m, 1H)

HPLC: $R_t$=3.3 min.

MS (ESIpos): m/z=464 (M+H)$^+$ (free base).

Example 10

N-[(3R)-1-Azabicyclo[2.2.2]oct-3-yl]-6-({[(2-nitrophenyl)amino]carbonyl}amino)-1-benzothiophene-2-carboxamide hydrochloride

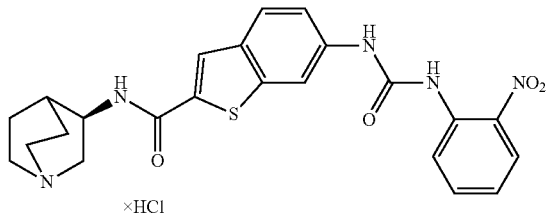 [SMILES: O=C(Nc1ccc2cc(C(=O)N[C@H]3CN4CCC3CC4)sc2c1)Nc1ccccc1[N+](=O)[O-]]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 35.1 mg (0.21 mmol) of 2-nitrophenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 6 mg (11.2% of theory) of the title compound are obtained.

$^1$H-NMR (400 MHz, Methanol-$d_4$): δ=8.51 (d, 1H), 8.30 (s, 1H), 8.20 (d, 1H), 8.01 (s, 1H), 7.85 (d, 1H), 7.69 (dd, 1H), 7.45 (d, 1H), 7.20 (dd, 1H), 4.45 (m, 1H), 3.86 (m, 1H), 3.52-3.10 (m, 5H), 2.39 (m, 1H), 2.28 (m, 1H), 2.11 (m, 2H), 1.97 (m, 1H)

HPLC: $R_t$=4.1 min.

MS (ESIpos): m/z=466 (M+H)$^+$ (free base).

Example 11

N-[(3R)-1-Azabicyclo[2.2.2]oct-3-yl]-6-({[(2,6-difluorophenyl)amino]carbonyl}-amino)-1-benzothiophene-2-carboxamide hydrochloride

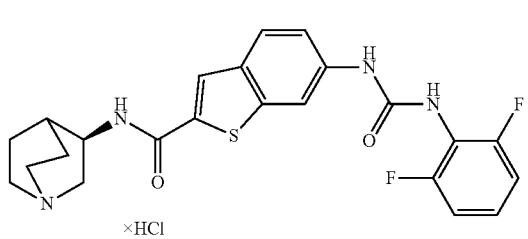 [SMILES: O=C(Nc1ccc2cc(C(=O)N[C@H]3CN4CCC3CC4)sc2c1)Nc1c(F)cccc1F]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 33.2 mg (0.21 mmol) of 2,6-difluorophenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 40 mg (75.9% of theory) of the title compound are obtained.

$^1$H-NMR (400 MHz, Methanol-$d_4$): δ=8.18 (s, 1H), 8.01 (s, 1H), 7.83 (d, 1H), 7.41 (d, 1H), 7.30 (m, 1H), 7.06 (m, 2H), 4.43 (m, 1H), 3.85 (m, 1H), 3.52-3.22 (m, 5H), 2.39 (m, 1H), 2.28 (m, 1H), 2.11 (m, 2H), 1.97 (m, 1H)

HPLC: $R_t$=3.8 min.

MS (ESIpos): m/z=457 (M+H)$^+$ (free base).

Example 12

N-[(3R)-1-Azabicyclo[2.2.2]oct-3-yl]-6-({[(2,4-dichlorophenyl)amino]carbonyl}-amino)-1-benzothiophene-2-carboxamide hydrochloride

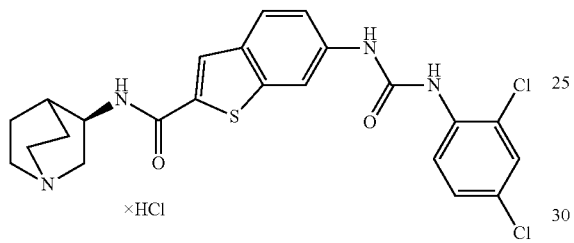

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 40.2 mg (0.21 mmol) of 2,4-dichlorophenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum, 25 mg (44.5% of theory) of the title compound are obtained.

$^1$H-NMR (400 MHz, Methanol-$d_4$): δ=8.26 (s, 1H), 8.19 (d, 1H), 8.01 (s, 1H), 7.83 (d, 1H), 7.49 (m, 1H), 7.38 (d, 1H), 7.31 (d, 1H), 4.43 (m, 1H), 3.85 (m, 1H), 3.51-3.18 (m, 5H), 2.38 (m, 1H), 2.27 (m, 1H), 2.10 (m, 2H), 1.96 (m, 1H)

HPLC: $R_t$=4.4 min.

MS (ESIpos): m/z=489 (M+H)$^+$ (free base).

Example 13

N-[(3R)-1-Azabicyclo[2.2.2]oct-3-yl]-6-[({[3-(trifluoromethyl)phenyl]amino}-carbonyl)amino]-1-benzothiophene-2-carboxamide hydrochloride

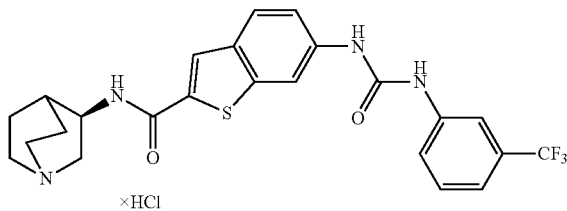 [SMILES: O=C(Nc1cccc(C(F)(F)F)c1)Nc1ccc2cc(C(=O)N[C@H]3CN4CCC3CC4)sc2c1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 40.0 mg (0.21 mmol) of 3-trifluoromethylphenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 51 mg (89% of theory) of the title compound are obtained.

$^1$H-NMR (400 MHz, Methanol-$d_4$): δ=8.22 (s, 1H), 8.04 (s, 1H), 7.93 (s, 1H), 7.83 (d, 1H), 7.63 (d, 1H), 7.49 (dd, 1H), 7.40 (m, 1H), 7.31 (d, 1H), 4.44 (m, 1H), 3.84 (m, 1H), 3.54-3.25 (m, 5H), 2.38 (m, 1H), 2.28 (m, 1H), 2.10 (m, 2H), 1.97 (m, 1H)

HPLC: $R_t$=4.3 min.

MS (ESIpos): m/z=489 (M+H)$^+$ (free base).

Example 14

N-[(3R)-1-Azabicyclo[2.2.2]oct-3-yl]-6-({[[(3,4,5-trimethoxyphenyl)amino]-carbonyl}amino)-1-benzothiophene-2-carboxamide hydrochloride

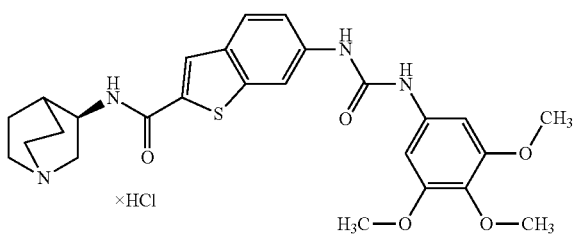 [SMILES: COc1cc(NC(=O)Nc2ccc3cc(C(=O)N[C@H]4CN5CCC4CC5)sc3c2)cc(OC)c1OC]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF is mixed with 29.8 μl (0.21 mmol) of triethylamine and 44.7 mg (0.21 mmol) of 3,4,5-trimethoxyphenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 11 mg (17.4% of theory) of the title compound are obtained.

$^1$H-NMR (400 MHz, Methanol-$d_4$): δ=8.22 (s, 1H), 8.00 (s, 1H), 7.82 (d, 1H), 7.38 (d, 1H), 6.82 (s, 2H), 4.43 (m, 1H), 3.85 (m, 7H), 3.73 (s, 3H), 3.52-3.18 (m, 5H), 2.39 (m, 1H), 2.28 (m, 1H), 2.10 (m, 2H), 1.96 (m, 1H)

HPLC: $R_t$=3.8 min.

MS (ESIpos): m/z=511 (M+H)$^+$ (free base).

Example 15

N-[(3R)-1-Azabicyclo[2.2.2]oct-3-yl]-6-[({[4-methoxy-3-(trifluoromethyl)phenyl]amino}carbonyl)amino]-1-benzothiophene-2-carboxamide hydrochloride

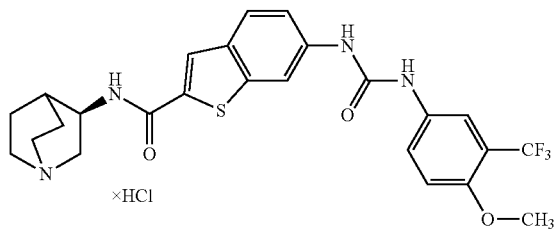 [SMILES: COc1ccc(NC(=O)Nc2ccc3cc(C(=O)N[C@H]4CN5CCC4CC5)sc3c2)cc1C(F)(F)F]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF and 0.2 ml of DMF is mixed with 29.8 µl (0.21 mmol) of triethylamine and 46.4 mg (0.21 mmol) of 4-methoxy-3-trifluoromethylphenyl isocyanate. After 18 h at room temperature, the product is purified by preparative HPLC. The concentrated product fraction is dissolved in a mixture of methanol and 1 N hydrochloric acid (2:1), again concentrated and dried under high vacuum. 15 mg (25.3% of theory) of the title compound are obtained.

$^1$H-NMR (300 MHz, Methanol-d$_4$): δ=8.18 (d, 1H), 8.02 (s, 1H), 7.81 (d, 1H), 7.73 (d, 1H), 7.60 (dd, 1H), 7.37 (dd, 1H), 7.13 (d, 1H), 4.43 (m, 1H), 3.87 (s, 3H), 3.83 (m, 1H), 3.53-3.17 (m, 5H), 2.38 (m, 1H), 2.27 (m, 1H), 2.10 (m, 2H), 1.96 (m, 1H)

HPLC: R$_t$=4.2 min.

MS (ESIpos): m/z=519 (M+H)$^+$ (free base).

Example 16

N-[(3R)-1-Azabicyclo[2.2.2]oct-3-yl]-6-[({[(3-methoxyphenyl]amino}carbonyl)-amino]-1-benzothiophene-2-carboxamide hydrochloride

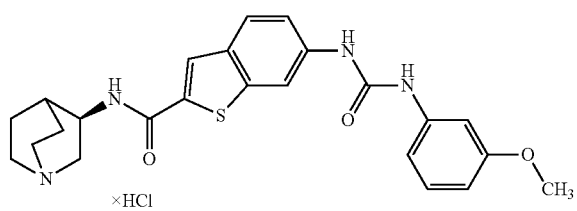 [SMILES: COc1cccc(NC(=O)Nc2ccc3cc(C(=O)N[C@H]4CN5CCC4CC5)sc3c2)c1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF and 0.2 ml of DMF is mixed with 29.8 µl (0.21 mmol) of triethylamine and 31.9 mg (0.21 mmol) of 3-methoxyphenyl isocyanate. After 18 h at room temperature, the product is purified by preparative HPLC. The concentrated product fraction is dissolved in a mixture of methanol and 1 N hydrochloric acid (2:1), again concentrated and dried under high vacuum. 17 mg (32.7% of theory) of the title compound are obtained.

$^1$H-NMR (300 MHz, Methanol-d$_4$): δ=8.20 (d, 1H), 8.02 (s, 1H), 7.81 (d, 1H), 7.37 (dd, 1H), 7.08 (m, 2H), 6.93 (m, 1H), 6.61 (m, 1H), 4.43 (m, 1H), 3.83 (m, 1H), 3.79 (s, 3H), 3.53-3.15 (m, 5H), 2.38 (m, 1H), 2.27 (m, 1H), 2.10 (m, 2H), 1.95 (m, 1H)

HPLC: R$_t$=4.0 min.

MS (ESIpos): m/z=451 (M+H)$^+$ (free base).

Example 17

N-[(3R)-1-Azabicyclo[2.2.2]oct-3-yl]-6-[{([3-trifluoromethoxyphenyl]amino}-carbonyl)amino]-1-benzothiophene-2-carboxamide hydrochloride

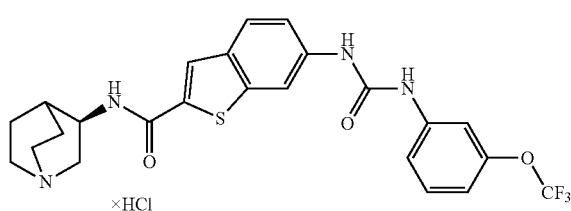 [SMILES: O=C(Nc1cccc(OC(F)(F)F)c1)Nc1ccc2cc(C(=O)N[C@H]3CN4CCC3CC4)sc2c1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THE and 0.2 ml of DMF is mixed with 29.8 µl (0.21 mmol) of triethylamine and 43.4 mg (0.21 mmol) of 3-trifluoromethoxyphenyl isocyanate. After 18 h at room temperature, the product is purified by preparative HPLC. The concentrated product fraction is dissolved in a mixture of methanol and 1 N hydrochloric acid (2:1), again concentrated and dried under high vacuum, 8.5 mg (14.7% of theory) of the title compound are obtained.

$^1$H-NMR (300 MHz, Methanol-d$_4$): δ=8.21 (d, 1H), 8.01 (s, 1H), 7.83 (d, 1H), 7.62 (s, 1H), 7.85 (m, 3H), 6.92 (m, 1H), 4.45 (m, 1H), 3.84 (m, 1H), 3.56-3.06 (m, 5H), 2.38 (m, 1H), 2.28 (m, 1H), 2.10 (m, 2H), 1.96 (m, 1H)

HPLC: R$_t$=4.4 min.

MS (ESIpos): m/z=505 (M+H)$^+$ (free base).

Example 18

N-[(3R)-1-Azabicyclo[2.2.2]oct-3-yl]-6-{[(tert-butylamino)carbonyl]amino}-1-benzothiophene-2-carboxamide hydrochloride

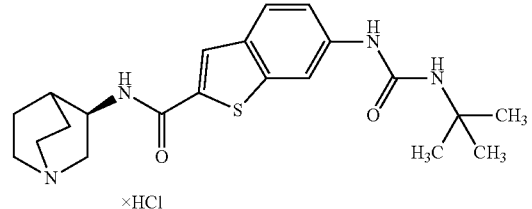 [SMILES: CC(C)(C)NC(=O)Nc1ccc2cc(C(=O)N[C@H]3CN4CCC3CC4)sc2c1]

A solution of 50 mg (0.13 mmol) of 6-amino-N-[(3R)-1-azabicyclo[2.2.2]oct-3-yl]-1-benzothiophene-2-carboxamide dihydrochloride in 2 ml of THF and 0.2 ml of DMF is mixed with 37.2 (0.27 mmol) of triethylamine and 26.5 mg (0.27 mmol) of tert-butyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 19 mg (32.6% of theory) of the title compound are obtained.

$^1$H-NMR (400 MHz, Methanol-d$_4$): δ=8.08 (m, 1H), 7.98 (s, 1H), 7.75 (d, 1H), 7.23 (dd, 1H), 4.43 (m, 1H), 3.83 (m, 1H), 3.50-3.18 (m, 5H), 2.38 (m, 1H), 2.27 (m, 1H), 2.10 (m, 2H), 1.95 (m, 1H), 1.38 (m, 9H)

HPLC: R$_t$=3.8 min.

MS (ESIpos): m/z=401 (M+H)$^+$ (free base).

Example 19

N-[(3R)-1-Azabicyclo[2.2.2]oct-3-yl]-6-{[(cyclohexylamino)carbonyl]amino}-1-benzothiophene-2-carboxamide hydrochloride

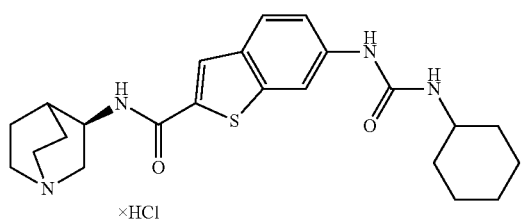 [SMILES: O=C(Nc1ccc2cc(C(=O)N[C@H]3CN4CCC3CC4)sc2c1)NC1CCCCC1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF and 0.2 ml of DMF is mixed with 29.8 µl (0.21 mmol) of triethylamine and 26.8 mg (0.21 mmol) of cyclohexyl isocyanate. After 18 h at room temperature, the product is purified by preparative HPLC. The concentrated product fraction is dissolved in a mixture of methanol and 1 N hydrochloric acid (2:1), again concentrated and dried under high vacuum. 23.4 mg (47.3% of theory) of the title compound are obtained.

$^1$H-NMR (300 MHz, Methanol-d$_4$): δ=8.10 (d, 1H), 7.99 (s, 1H), 7.77 (d, 1H), 7.27 (dd, 1H), 4.43 (m, 1H), 3.82 (m, 1H), 3.64-3.10 (m, 6H), 2.37 (m, 1H), 2.28 (m, 1H), 2.09 (m, 2H), 1.94 (m, 3H), 1.76 (m, 2H), 1.62 (m, 1H), 1.40 (m, 2H), 1.26 (m, 3H)

HPLC: R$_t$=4.0 min.

MS (ESIpos): m/z=427 (M+H)$^+$ (free base).

Example 20

N-[(3R)-1-Azabicyclo[2.2.2]oct-3-yl]-6-[({[(1S)-1-phenylethyl]amino}carbonyl)-amino]-1-benzothiophene-2-carboxamide hydrochloride

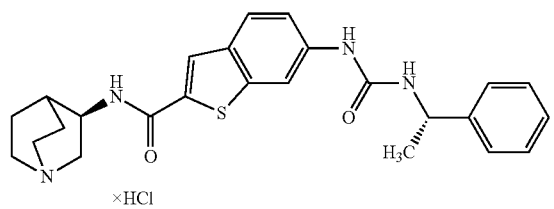 [SMILES: C[C@H](NC(=O)Nc1ccc2cc(C(=O)N[C@H]3CN4CCC3CC4)sc2c1)c1ccccc1]

A solution of 40 mg (0.11 mmol) of 6-amino-N-[(3R)-1-azabicyclo[2.2.2]oct-3-yl]-1-benzothiophene-2-carboxamide dihydrochloride in 2 ml of THF and 0.2 ml of DMF is mixed with 29.8 µl (0.21 mmol) of triethylamine and 31.5 mg (0.21 mmol) of (S)-(−)-α-methylbenzyl isocyanate. After 18 h at room temperature, the product is purified by preparative HPLC. The concentrated product fraction is dissolved in a mixture of methanol and 1 N hydrochloric acid (2:1), again concentrated and dried under high vacuum. 32.5 mg (62.7% of theory) of the title compound are obtained.

$^1$H-NMR (400 MHz, Methanol-d$_4$): δ=8.10 (s, 1H), 7.99 (m, 2H), 7.77 (d, 1H), 7.39-7.20 (m, 5H), 4.93 (q, 1H), 4.43 (m, 1H), 3.83 (m, 1H), 3.47 (m, 1H), 3.42-3.26 (m, 4H), 2.37 (m, 1H), 2.27 (m, 1H), 2.09 (m, 2H), 1.95 (m, 1H), 1.49 (d, 3H)

HPLC: R$_t$=4.0 min.

MS (ESIpos): m/z=449 (M+H)$^+$ (free base).

Example 21

7-[(Anilinocarbonyl)amino]-N-[(3R)-1-azabicyclo[2.2.2]oct-3-yl]-1-benzothiophene-2-carboxamide hydrochloride

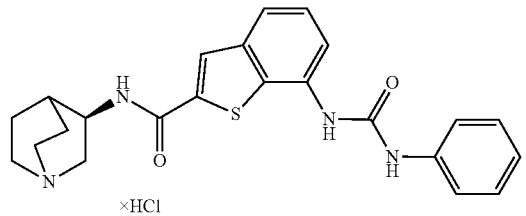 [SMILES: O=C(Nc1ccccc1)Nc1cccc2cc(C(=O)N[C@H]3CN4CCC3CC4)sc12]

A solution of 44 mg (0.12 mmol) of 7-amino-N-[(3R)-1-azabicyclo[2.2.2]oct-3-yl]-1-benzothiophene-2-carboxamide dihydrochloride in 2 ml of THF is mixed with 32.8 µl (0.24 mmol) of triethylamine and 28 mg (0.24 mmol) of phenyl isocyanate. After 18 h at room temperature, the product is purified by preparative HPLC. The concentrated product fraction is dissolved in a mixture of acetonitrile and 1 N hydrochloric acid (5:1), again concentrated and dried under high vacuum. 20 mg (36.1% of theory) of the title compound are obtained.

$^1$H-NMR (400 MHz, Methanol-d$_4$): δ=8.12 (s, 1H), 7.80 (d, 1H), 7.70 (d, 1H), 7.47 (m, 3H), 7.30 (m, 2H), 7.05 (m, 1H), 4.45 (m, 1H), 3.84 (m, 1H), 3.73 (s, 3H), 3.53-3.21 (m, 5H), 2.39 (m, 1H), 2.28 (m, 1H), 2.10 (m, 2H), 1.96 (m, 1H)

HPLC: R$_t$=3.9 min.

MS (ESIpos): m/z=421 (M+H)$^+$ (free base).

Example 22

N-[(3R)-1-Azabicyclo[2.2.2]oct-3-yl]-6-({[(4-methoxyphenyl)amino]carbonyl}-amino)-1-benzofuran-2-carboxamide hydrochloride

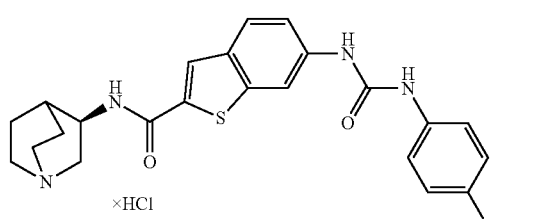

50 mg (0.18 mmol) of 6-amino-N-[(3R)-1-azabicyclo[2.2.2]oct-3-yl]-1-benzofuran-2-carboxamide are introduced into 3 ml of THF/DMF (10:1), and 73 μl (0.53 mmol) of triethylamine and 78.4 mg (0.53 mmol) of 4-methoxyphenyl isocyanate are added. After 18 h at room temperature and a further 20 h at 50° C., the contents of the flask are concentrated in vacuo. After redissolving in a little DMSO and adding water, the resulting precipitate is filtered off with suction. The solid is dissolved in DMF/water and purified by preparative HPLC. The concentrated product fraction is dissolved in a mixture of methanol and 1 N hydrochloric acid in diethyl ether (5:1), again concentrated and dried under high vacuum. 5.3 mg (7% of theory) of the title compound are obtained.

$^1$H-NMR (300 MHz, Methanol-d$_4$): δ=8.07 (s, 1H), 7.60 (m, 1H), 7.47 (s, 1H), 7.33 (m, 2H), 7.12 (dd, 1H), 6.88 (m, 2H), 4.49 (m, 1H), 3.82 (m, 1H), 3.77 (s, 3H), 3.54-3.18 (m, 5H), 2.37 (m, 1H), 2.25 (m, 1H), 2.10 (m, 2H), 1.96 (m, 1H)

HPLC: R$_t$=3.8 mm.

MS (ESIpos): m/z=435 (M+H)$^+$ (free base).

The invention claimed is:

1. A method of treating a cognitive impairment in a patient in need thereof, comprising administering to the patient a compound represented by Formula (I):

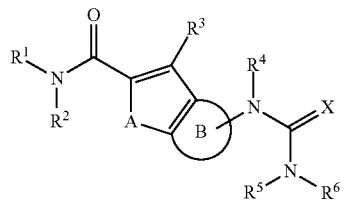

wherein:
R$^1$ represents 1-azabicyclo[2.2.2]oct-3-yl;
R$^2$ represents hydrogen or C$_1$-C$_6$-alkyl;
R$^3$ represents hydrogen, halogen, amino, hydroxy or C$_1$-C$_6$-alkyl;
R$^4$ represents hydrogen or C$_1$-C$_6$-alkyl which is optionally substituted by a radical selected from the group of hydroxy, halogen, cyano, C$_1$-C$_6$-alkoxy, trifluoromethyl, or trifluoromethoxy;
R$^5$ represents hydrogen or C$_1$-C$_6$-alkyl; or R$^4$ and R$^5$ together with the nitrogen atom to which they are bonded are a 5- to 6-membered heterocycle which is optionally substituted by up to 2 substituents independently of one another selected from the group of C$_1$-C$_6$-alkyl, C$_1$-C$_4$-acyl, oxo, thioxo;
R$^6$ represents (i) hydrogen, (ii) C$_1$-C$_6$-alkyl, (iii) C$_3$-C$_8$-cycloalkyl, (iv) C$_6$-C$_{10}$-aryl, (v) 5- to 10-membered heteroaryl, or (vi) C$_6$-C$_{10}$-arylcarbonyl, where (ii) is optionally substituted by phenyl, C$_1$-C$_6$-alkoxycarbonyl or C$_1$-C$_6$-alkoxy, and (iv), (v) and (vi) are optionally substituted by up to 3 radicals selected independently of one another from the group of C$_1$-C$_6$-alkyl, C$_1$-C$_6$-hydroxyalkyl, 3- to 8-membered heterocyclyl, C$_6$-C$_{10}$-aryl, 5- to 10-membered heteroaryl, hydroxy, halogen, cyano, C$_1$-C$_6$-alkoxy, C$_1$-C$_6$-acyl, trifluoromethyl, trifluoromethoxy, nitro, amino, C$_1$-C$_6$-alkylamino, or C$_1$-C$_6$-acylamino; or R$^5$ and R$^6$ together with the nitrogen atom to which they are bonded are a 3- to 10-membered heterocycle which is optionally substituted by C$_1$-C$_6$-alkyl or C$_1$-C$_6$-hydroxyalkyl;
A represents oxygen or sulfur;
X represents oxygen or sulfur;
ring B represents benzo which is optionally substituted by radicals from the series halogen, cyano, trifluoromethyl, trifluoromethoxy, nitro, amino, C$_1$-C$_6$-alkyl and C$_1$-C$_6$-alkoxy;
or a salt thereof.

2. The method of claim 1, wherein:
R$^6$ represents (i) hydrogen, (ii) C$_1$-C$_6$-alkyl, (iii) C$_3$-C$_8$-cycloalkyl, (iv) C$_6$-C$_{10}$-aryl, or (v) 5- to 10-membered heteroaryl, where (ii) is optionally substituted by phenyl, or C$_1$-C$_6$-alkoxy, and (iv) and (v) are optionally substituted by up to 3 radicals selected independently of one another from the group of C$_1$-C$_6$-alkyl, C$_1$-C$_6$-hydroxyalkyl, 3- to 8-membered heterocyclyl, C$_6$-C$_{10}$-aryl, 5- to 10-membered heteroaryl, hydroxy, halogen, cyano, C$_1$-C$_6$-alkoxy, C$_1$-C$_6$-acyl, trifluoromethyl, trifluoromethoxy, nitro, amino, C$_1$-C$_6$-alkylamino, or C$_1$-C$_6$-acylamino; or R$^5$ and R$^6$ together with the nitrogen atom to which they are bonded are a 3- to 8-membered heterocycle which is optionally substituted by C$_1$-C$_6$-alkyl or C$_1$-C$_6$-hydroxyalkyl; and
A represents oxygen.

3. The method of claim 1, wherein:
R$^2$ represents hydrogen or C$_1$-C$_4$-alkyl:
R$^3$ represents hydrogen, halogen, amino, hydroxy or C$_1$-C$_4$-alkyl;
R$^4$ represents hydrogen or C$_1$-C$_4$-alkyl which is optionally substituted by a radical selected from the group of hydroxy, halogen, cyano, C$_1$-C$_3$-alkoxy, trifluoromethyl or trifluoromethoxy;
R$^5$ represents hydrogen or C$_1$-C$_4$-alkyl, or R$^4$ and R$^5$ together with the nitrogen atom to which they are bonded are a 5- to 6-membered heterocycle which is optionally substituted by up to 2 substituents independently of one another selected from the group of C$_1$-C$_6$-alkyl, C$_1$-C$_4$-acyl, oxo, thioxo;
R$^6$ represents (i) hydrogen, (ii) C$_1$-C$_4$-alkyl, (iii) C$_5$-C$_6$-cycloalkyl, (iv) phenyl, (v) 5- to 6-membered heteroaryl, or (vi) C$_6$-C$_{10}$-arylcarbonyl, where (ii) is optionally substituted by phenyl, C$_1$-C$_4$-alkoxycarbonyl or C$_1$-C$_3$-alkoxy, and (iv), (v) and (vi) are optionally substituted by up to 3 radicals selected independently of one another from the group of C$_1$-C$_4$-alkyl, C$_1$-C$_4$-hydroxyalkyl, 3- to 8-membered heterocyclyl, C$_6$-C$_{10}$-aryl, 5- to 10-membered heteroaryl, hydroxy, fluorine, chlorine, cyano, C$_1$-C$_3$-alkoxy, C$_1$-C$_3$-acyl, trifluoromethyl, trifluoromethoxy, nitro, amino, C$_1$-C$_3$-alkylamino, or C$_1$-C$_3$-acylamino, or R$^5$ and R$^6$ together with the nitrogen atom to which they are bonded are a 3- to 10-membered heterocycle which is optionally substituted by C$_1$-C$_3$-alkyl or C$_1$-C$_3$-hydroxyalkyl;
A represents oxygen;
X represents oxygen; and
ring B represents benzo which is optionally substituted by radicals from the series chlorine, fluorine, cyano, trifluoromethyl, trifluoromethoxy, amino, C$_1$-C$_4$-alkyl and C$_1$-C$_4$-alkoxy.

4. The method of claim 3, wherein:
R$^4$ represents hydrogen or C$_1$-C$_4$-alkyl which is optionally substituted by a radical selected from the group of hydroxy, C$_1$-C$_3$-alkoxy, trifluoromethyl, trifluoromethoxy; and
R$^6$ represents (i) hydrogen, (ii) C$_1$-C$_4$-alkyl, (iii) C$_5$-C$_6$-cycloalkyl, (iv) phenyl, or (v) 5- to 6-membered heteroaryl, where (ii) is optionally substituted by phenyl, and (iv) and (v) are optionally substituted by up to 3 radicals selected independently of one another from the group of C$_1$-C$_4$-alkyl, C$_1$-C$_4$-hydroxyalkyl, hydroxy, chlorine, fluorine, cyano, $C_1$-$C_3$-alkoxy, $C_1$-$C_6$-acyl, trifluoromethyl, trifluoromethoxy, amino, $C_1$-$C_3$-alkylamino, or $C_1$-$C_3$-acylamino, or $R^5$ and $R^6$ together with the nitrogen atom to which they are bonded are a 5- to 6-membered heterocycle which is optionally substituted by $C_1$-$C_3$-alkyl or $C_1$-$C_3$-hydroxyalkyl.

5. The method of claim 1, wherein:
$R^2$-$R^4$ each represents hydrogen;
$R^5$ represents hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_4$-alkyl, $C_1$-$C_4$-acyl, oxo, thioxo;
$R^6$ represents (i) hydrogen, (ii) $C_1$-$C_4$-alkyl, (iii) $C_5$-$C_6$-cycloalkyl, (iv) phenyl, (v) pyridyl, (vi) $C_6$-$C_{10}$-arylcarbonyl, where (ii) is optionally substituted by phenyl, $C_1$-$C_4$-alkoxycarbonyl or $C_1$-$C_3$-alkoxy, and (iv), (v) and (vi) are optionally substituted by up to 3 radicals selected independently of one another from the group of $C_1$-$C_4$-alkyl, $C_1$-$C_4$-hydroxyalkyl, 3- to 8-membered heterocyclyl, $C_6$-$C_{10}$-aryl, 5- to 10-membered heteroaryl, hydroxy, fluorine, chlorine, cyano, $C_1$-$C_3$-alkoxy, $C_1$-$C_3$-acyl, trifluoromethyl, trifluoromethoxy, nitro, amino, $C_1$-$C_3$-alkylamino, or $C_1$-$C_3$-acylamino, or $R^5$ and $R^6$ together with the nitrogen atom to which they are bonded are a 3- to 10-membered heterocycle which is optionally substituted by $C_1$-$C_3$-alkyl or $C_1$-$C_3$-hydroxyalkyl;
A represents oxygen;
X represents oxygen; and
ring B represents benzo.

6. The method of claim 1, wherein:
$R^2$ represents hydrogen;
$R^3$ represents hydrogen, chlorine, fluorine, amino or $C_1$-$C_3$-alkyl;
$R^4$ represents hydrogen, methyl or ethyl, where methyl and ethyl are optionally substituted by a radical selected from the group of hydroxy, methoxy, ethoxy, trifluoromethyl, trifluoromethoxy, or $R^4$ and $R^5$ together with the nitrogen atom to which they are bonded are a 5- to 6-membered heterocycle which is optionally substituted by up to 2 substituents independently of one another selected from the group of $C_1$-$C_3$-alkyl, $C_1$-$C_4$-acyl, oxo, thioxo;
$R^5$ represents hydrogen or $C_1$-$C_3$-alkyl;
$R^6$ represents (i) hydrogen, (ii) $C_1$-$C_4$-alkyl, (iii) cyclopentyl, cyclohexyl, (iv) phenyl, (v) benzyl, or (vi) phenethyl, where (iv) to (vi) are optionally substituted by up to 3 radicals selected independently of one another from the group of hydroxy, chlorine, fluorine, cyano, methoxy, ethoxy, $C_1$-$C_4$-acyl, trifluoromethyl, trifluoromethoxy, amino, $C_1$-$C_3$-alkylamino;
A represents oxygen;
X represents oxygen; and
ring B represents benzo which is optionally substituted by radicals from the series chlorine, fluorine, cyano, trifluoromethyl, trifluoromethoxy, $C_1$-$C_4$-alkyl, methoxy and ethoxy.

7. The method of claim 1, wherein the cognitive impairment is Alzheimer's disease.

8. The method of claim 1, wherein the cognitive impairment is Schizophrenia.

9. The method of claim 1, wherein the method improves perception, concentration, learning, or memory.

10. The method of claim 1, wherein the compound, or salt thereof, is selected from the group consisting of:

6-[(Anilino carbonyl)amino]-N-[(3R)-1-azabicyclo[2.2.2]oct-3-yl]-1-benzothiophene-2-carboxamide hydrochloride;
N-[(3R)-1-Azabicyclo[2.2.2]oct-3-yl]-6-({[(4-chlorophenyl)amino]carbonyl}amino)-1-benzothiophene-2-carboxamide hydrochloride;
N-[(3R)-1-Azabicyclo[2.2.2]oct-3-yl]-6-({[(2-methoxyphenyl)amino]carbonyl}-amino)-1-benzothiophene-2-carboxamide hydrochloride;
N-[(3R)-1-Azabicyclo[2.2.2]oct-3-yl]-6-({[(4-methoxyphenyl)amino]carbonyl}-amino)-1-benzothiophene-2-carboxamide hydrochloride;
N-[(3R)-1-Azabicyclo[2.2.2]oct-3-yl]-6-({[(2-phenylethyl)amino]carbonyl}amino)-1-benzothiophene-2-carboxamide hydrochloride;
N-[(3R)-1-Azabicyclo[2.2.2]oct-3-yl]-6-({[(3-cyanophenyl)amino]carbonyl}amino)-1-benzothiophene-2-carboxamide hydrochloride;
N-[(3R)-1-Azabicyclo[2.2.2]oct-3-yl]-6-({[(3-bromophenyl)amino]carbonyl}amino)-1-benzothiophene-2-carboxamide hydrochloride;
N-[(3R)-1-Azabicyclo[2.2.2]oct-3-yl]-6-({[(2-ethoxyphenyl)amino]carbonyl}amino)-1-benzothiophene-2-carboxamide hydrochloride;
N-[(3R)-1-Azabicyclo[2.2.2]oct-3-yl]-6-({[(4-(dimethylamino)phenyl)amino]-carbonyl}amino)-1-benzothiophene-2-carboxamide hydrochloride;
N-[(3R)-1-Azabicyclo[2.2.2]oct-3-yl]-6-({[(2-nitrophenyl)amino]carbonyl}amino)-1-benzothiophene-2-carboxamide hydrochloride;
N-[(3R)-1-Azabicyclo[2.2.2]oct-3-yl]-6-({[(2,6-difluorophenyl)amino]carbonyl}-amino)-1-benzothiophene-2-carboxamide hydrochloride;
N-[(3R)-1-Azabicyclo[2.2.2]oct-3-yl]-6-({[(2,4-dichlorophenyl)amino]carbonyl}-amino)-1-benzothiophene-2-carboxamide hydrochloride;
N-[(3R)-1-Azabicyclo[2.2.2]oct-3-yl]-6-[({[3-(trifluoromethyl)phenyl]amino)-carbonyl}amino]-1-benzothiophene-2-carboxamide hydrochloride;
N-[(3R)-1-Azabicyclo[2.2.2]oct-3-yl]-6-({[(3,4,5-trimethoxyphenyl)amino]-carbonyl}amino)-1-benzothiophene-2-carboxamide hydrochloride;
N-[(3R)-1-Azabicyclo[2.2.2]oct-3-yl]-6-[({[4-methoxy-3-(trifluoromethyl)phenyl]-amino}carbonyl)amino]-1-benzothiophene-2-carboxamide hydrochloride;
N-[(3R)-1-Azabicyclo[2.2.2]oct-3-yl]-6-[({[3-methoxyphenyl]amino}carbonyl)-amino]-1-benzothiophene-2-carboxamide hydrochloride;
N-[(3R)-1-Azabicyclo[2.2.2]oct-3-yl]-6-[({[3-trifluoromethoxyphenyl]amino}-carbonyl)amino]-1-benzothiophene-2-carboxamide hydrochloride;
N-[(3R)-1-Azabicyclo[2.2.2]oct-3-yl]-6-{[(tert-butylamino)carbonyl]amino}-1-benzothiophene-2-carboxamide hydrochloride;
N-[(3R)-1-Azabicyclo[2.2.2]oct-3-yl]-6-{[(cyclohexylamino)carbonyl]amino}-1-benzothiophene-2-carboxamide hydrochloride;
N-[(3R)-1-Azabicyclo[2.2.2]oct-3-yl]-6-[({[(1S)-1-phenylethyl]amino}carbonyl)-amino]-1-benzothiophene-2-carboxamide hydrochloride;
7-[(Anilinocarbonyl)amino]-N-[(3R)-1-azabicyclo[2.2.2]oct-3-yl]-1-benzothiophene-2-carboxamide hydrochloride; and
N-[(3R)-1-Azabicyclo[2.2.2]oct-3-yl]-6-({[(4-methoxyphenyl)amino]carbonyl}-amino)-1-benzofuran-2-carboxamide hydrochloride.

11. The method of claim 10, wherein the cognitive impairment is Alzheimer's disease.

12. The method of claim 10, wherein the cognitive impairment is Schizophrenia.

13. The method of claim 10, wherein the method improves perception, concentration, learning, or memory.

14. A method of treating a cognitive impairment in a patient in need thereof, comprising administering to the patient a pharmaceutical composition comprising:
   i) a compound represented by Formula (I):

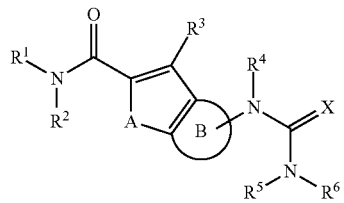

wherein:
   $R^1$ represents 1-azabicyclo[2.2.2]oct-3-yl;
   $R^2$ represents hydrogen or $C_1$-$C_6$-alkyl:
   $R^3$ represents hydrogen, halogen, amino, hydroxy or $C_1$-$C_6$-alkyl;
   $R^4$ represents hydrogen or $C_1$-$C_6$-alkyl which is optionally substituted by a radical selected from the group of hydroxy, halogen, cyano, $C_1$-$C_6$-alkoxy, trifluoromethyl, or trifluoromethoxy;
   $R^5$ represents hydrogen or $C_1$-$C_6$-alkyl; or $R^4$ and $R^5$ together with the nitrogen atom to which they are bonded are a 5- to 6-membered heterocycle which is optionally substituted by up to 2 substituents independently of one another selected from the group of $C_1$-$C_6$-alkyl, $C_1$-$C_4$-acyl, oxo, thioxo;
   $R^6$ represents (i) hydrogen, (ii) $C_1$-$C_6$-alkyl, (iii) $C_3$-$C_8$-cycloalkyl, (iv) $C_6$-$C_{10}$-aryl, (v) 5- to 10-membered heteroaryl, or (vi) $C_6$-$C_{10}$-arylcarbonyl, where (ii) is optionally substituted by phenyl, $C_1$-$C_6$-alkoxycarbonyl or $C_1$-$C_6$-alkoxy, and (iv), (v) and (vi) are optionally substituted by up to 3 radicals selected independently of one another from the group of $C_1$-$C_6$-alkyl, $C_1$-$C_6$-hydroxyalkyl, 3- to 8-membered heterocyclyl, $C_6$-$C_{10}$-aryl, 5- to 10-membered heteroaryl, hydroxy, halogen, cyano, $C_1$-$C_6$-alkoxy, $C_1$-$C_6$-acyl, trifluoromethyl, trifluoromethoxy, nitro, amino, $C_1$-$C_6$-alkylamino, or $C_1$-$C_6$-acylamino; or $R^5$ and $R^6$ together with the nitrogen atom to which they are bonded are a 3- to 10-membered heterocycle which is optionally substituted by $C_1$-$C_6$-alkyl or $C_1$-$C_6$-hydroxyalkyl;
   A represents oxygen or sulfur;
   X represents oxygen or sulfur;
   ring B represents benzo which is optionally substituted by radicals from the series halogen, cyano, trifluoromethyl, trifluoromethoxy, nitro, amino, $C_1$-$C_6$-alkyl and $C_1$-$C_6$-alkoxy;
or a salt thereof; and
   ii) a pharmaceutically acceptable carrier.

15. The method of claim 14, wherein:
   $R^6$ represents (i) hydrogen, (ii) $C_1$-$C_6$-alkyl, (iii) $C_3$-$C_8$-cycloalkyl, (iv) $C_6$-$C_{10}$-aryl, or (v) 5- to 10-membered heteroaryl, where (ii) is optionally substituted by phenyl, or $C_1$-$C_6$-alkoxy, and (iv) and (v) are optionally substituted by up to 3 radicals selected independently of one another from the group of $C_1$-$C_6$-alkyl, $C_1$-$C_6$-hydroxyalkyl, 3- to 8-membered heterocyclyl, $C_6$-$C_{10}$-aryl, 5- to 10-membered heteroaryl, hydroxy, halogen, cyano, $C_1$-$C_6$-alkoxy, $C_1$-$C_6$-acyl, trifluoromethyl, trifluoromethoxy, nitro, amino, $C_1$-$C_6$-alkylamino, or $C_1$-$C_6$-acylamino; or $R^5$ and $R^6$ together with the nitrogen atom to which they are bonded are a 3- to 8-membered heterocycle which is optionally substituted by $C_1$-$C_6$-alkyl or $C_1$-$C_6$-hydroxyalkyl; and
   A represents oxygen.

16. The method of claim 14, wherein:
   $R^2$ represents hydrogen or $C_1$-$C_4$-alkyl;
   $R^3$ represents hydrogen, halogen, amino, hydroxy or $C_1$-$C_4$-alkyl;
   $R^4$ represents hydrogen or $C_1$-$C_4$-alkyl which is optionally substituted by a radical selected from the group of hydroxy, halogen, cyano, $C_1$-$C_3$-alkoxy, trifluoromethyl or trifluoromethoxy;
   $R^5$ represents hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_6$-alkyl, $C_1$-$C_4$-acyl, oxo, thioxo;
   $R^6$ represents (i) hydrogen, (ii) $C_1$-$C_4$-alkyl, (iii) $C_5$-$C_6$-cycloalkyl, (iv) phenyl, (v) 5- to 6-membered heteroaryl, or (vi) $C_6$-$C_{10}$-arylcarbonyl, where (ii) is optionally substituted by phenyl, $C_1$-$C_4$-alkoxycarbonyl or $C_1$-$C_3$-alkoxy, and (iv), (v) and (vi) are optionally substituted by up to 3 radicals selected independently of one another from the group of $C_1$-$C_4$-alkyl, $C_1$-$C_4$-hydroxyalkyl, 3- to 8-membered heterocyclyl, $C_6$-$C_{10}$-aryl, 5- to 10-membered heteroaryl, hydroxy, fluorine, chlorine, cyano, $C_1$-$C_3$-alkoxy, $C_1$-$C_3$-acyl, trifluoromethyl, trifluoromethoxy, nitro, amino, $C_1$-$C_3$-alkylamino, or $C_1$-$C_3$-acylamino, or $R^5$ and $R^6$ together with the nitrogen atom to which they are bonded are a 3- to 10-membered heterocycle which is optionally substituted by $C_1$-$C_3$-alkyl or $C_1$-$C_3$-hydroxyalkyl;
   A represents oxygen;
   X represents oxygen; and
   ring B represents benzo which is optionally substituted by radicals from the series chlorine, fluorine, cyano, trifluoromethyl, trifluoromethoxy, amino, $C_1$-$C_4$-alkyl and $C_1$-$C_4$-alkoxy.

17. The method of claim 14, wherein:
   $R^4$ represents hydrogen or $C_1$-$C_4$-alkyl which is optionally substituted by a radical selected from the group of hydroxy, $C_1$-$C_3$-alkoxy, trifluoromethyl, trifluoromethoxy; and
   $R^6$ represents (i) hydrogen, (ii) $C_1$-$C_4$-alkyl, (iii) $C_5$-$C_6$-cycloalkyl, (iv) phenyl, or (v) 5- to 6-membered heteroaryl, where (ii) is optionally substituted by phenyl, and (iv) and (v) are optionally substituted by up to 3 radicals selected independently of one another from the group of $C_1$-$C_4$-alkyl, $C_1$-$C_4$-hydroxyalkyl, hydroxy, chlorine, fluorine, cyano, $C_1$-$C_3$-alkoxy, $C_1$-$C_6$-acyl, trifluoromethyl, trifluoromethoxy, amino, $C_1$-$C_3$-alkylamino, or $C_1$-$C_3$-acylamino, or $R^5$ and $R^6$ together with the nitrogen atom to which they are bonded are a 5- to 6-membered heterocycle which is optionally substituted by $C_1$-$C_3$-alkyl or $C_1$-$C_3$-hydroxyalkyl.

18. The method of claim 14, wherein:
   $R^2$-$R^4$ each represents hydrogen;
   $R^5$ represents hydrogen or $C_1$-$C_4$-alkyl, or $R^4$ and $R^5$ together with the nitrogen atom to which they are bonded are a 5- to 6-membered heterocycle which is optionally substituted by up to 2 substituents independently of one another selected from the group of $C_1$-$C_4$-alkyl, $C_1$-$C_4$-acyl, oxo, thioxo;

$R^6$ represents (i) hydrogen, (ii) $C_1$-$C_4$-alkyl, (iii) $C_5$-$C_6$-cycloalkyl, (iv) phenyl, (v) pyridyl, (vi) $C_6$-$C_{10}$-arylcarbonyl, where (ii) is optionally substituted by phenyl, $C_1$-$C_4$-alkoxycarbonyl or $C_1$-$C_3$-alkoxy, and (iv), (v) and (vi) are optionally substituted by up to 3 radicals selected independently of one another from the group of $C_1$-$C_4$-alkyl, $C_1$-$C_4$-hydroxyalkyl, 3- to 8-membered heterocyclyl, $C_6$-$C_{10}$-aryl, 5- to 10-membered heteroaryl, hydroxy, fluorine, chlorine, cyano, $C_1$-$C_3$-alkoxy, $C_1$-$C_3$-acyl, trifluoromethyl, trifluoromethoxy, nitro, amino, $C_1$-$C_3$-alkylamino, or $C_1$-$C_3$-acylamino, or $R^5$ and $R^6$ together with the nitrogen atom to which they are bonded are a 3- to 10-membered heterocycle which is optionally substituted by $C_1$-$C_3$-alkyl or $C_1$-$C_3$-hydroxyalkyl;

A represents oxygen;

X represents oxygen; and ring B represents benzo.

19. The method of claim 14, wherein:

$R^2$ represents hydrogen;

$R^3$ represents hydrogen, chlorine, fluorine, amino or $C_1$-$C_3$-alkyl;

$R^4$ represents hydrogen, methyl or ethyl, where methyl and ethyl are optionally substituted by a radical selected from the group of hydroxy, methoxy, ethoxy, trifluoromethyl, trifluoromethoxy, or $R^4$ and $R^5$ together with the nitrogen atom to which they are bonded are a 5- to 6-membered heterocycle which is optionally substituted by up to 2 substituents independently of one another selected from the group of $C_1$-$C_3$-alkyl, $C_1$-$C_4$-acyl, oxo, thioxo;

$R^5$ represents hydrogen or $C_1$-$C_3$-alkyl;

$R^6$ represents (i) hydrogen, (ii) $C_1$-$C_4$-alkyl, (iii) cyclopentyl, cyclohexyl, (iv) phenyl, (v) benzyl, or (vi) phenethyl, where (iv) to (vi) are optionally substituted by up to 3 radicals selected independently of one another from the group of hydroxy, chlorine, fluorine, cyano, methoxy, ethoxy, $C_1$-$C_4$-acyl, trifluoromethyl, trifluoromethoxy, amino, $C_1$-$C_3$-alkylamino;

A represents oxygen;

X represents oxygen; and ring B represents benzo which is optionally substituted by radicals from the series chlorine, fluorine, cyano, trifluoromethyl, trifluoromethoxy, $C_1$-$C_4$-alkyl methoxy and ethoxy.

20. The method of claim 14, wherein the cognitive impairment is Alzheimer's disease.

21. The method of claim 14, wherein the cognitive impairment is Schizophrenia.

22. The method of claim 14, wherein the method improves perception, concentration, learning, or memory.

23. The method of claim 14, wherein the compound, or salt thereof, is selected from the group consisting of:

6-[(Anilino carbonyl)amino]-N-[(3R)-1-azabicyclo[2.2.2]oct-3-yl]-1-benzothiophene-2-carboxamide hydrochloride;

N-[(3R)-1-Azabicyclo[2.2.2]oct-3-yl]-6-({[(4-chlorophenyl)amino]carbonyl}amino)-1-benzothiophene-2-carboxamide hydrochloride;

N-[(3R)-1-Azabicyclo[2.2.2]oct-3-yl]-6-({[(2-methoxyphenyl)amino]carbonyl}-amino)-1-benzothiophene-2-carboxamide hydrochloride;

N-[(3R)-1-Azabicyclo[2.2.2]oct-3-yl]-6-({[(4-methoxyphenyl)amino]carbonyl}-amino)-1-benzothiophene-2-carboxamide hydrochloride;

N-[(3R)-1-Azabicyclo[2.2.2]oct-3-yl]-6-({[(2-phenylethyl)amino]carbonyl}amino)-1-benzothiophene-2-carboxamide hydrochloride;

N-[(3R)-1-Azabicyclo[2.2.2]oct-3-yl]-6-({[(3-cyanophenyl)amino]carbonyl}amino)-1-benzothiophene-2-carboxamide hydrochloride;

N-[(3R)-1-Azabicyclo[2.2.2]oct-3-yl]-6-({[(3-bromophenyl)amino]carbonyl}amino)-1-benzothiophene-2-carboxamide hydrochloride;

N-[(3R)-1-Azabicyclo[2.2.2]oct-3-yl]-6-({[(2-ethoxyphenyl)amino]carbonyl}amino)-1-benzothiophene-2-carboxamide hydrochloride;

N-[(3R)-1-Azabicyclo[2.2.2]oct-3-yl]-6-({[(4-(dimethylamino)phenyl)amino]-carbonyl}amino)-1-benzothiophene-2-carboxamide hydrochloride;

N-[(3R)-1-Azabicyclo[2.2.2]oct-3-yl]-6-({[(2-nitrophenyl)amino]carbonyl}amino)-1-benzothiophene-2-carboxamide hydrochloride;

N-[(3R)-1-Azabicyclo[2.2.2]oct-3-yl]-6-({[(2,6-difluorophenyl)amino]carbonyl}-amino)-1-benzothiophene-2-carboxamide hydrochloride;

N-[(3R)-1-Azabicyclo[2.2.2]oct-3-yl]-6-({[(2,4-dichlorophenyl)amino]carbonyl}-amino)-1-benzothiophene-2-carboxamide hydrochloride;

N-[(3R)-1-Azabicyclo[2.2.2]oct-3-yl]-6-[({[3-(trifluoromethyl)phenyl]amino}-carbonyl)amino]-1-benzothiophene-2-carboxamide hydrochloride;

N-[(3R)-1-Azabicyclo[2.2.2]oct-3-yl]-6-({[(3,4,5-trimethoxyphenyl)amino]-carbonyl}amino)-1-benzothiophene-2-carboxamide hydrochloride;

N-[(3R)-1-Azabicyclo[2.2.2]oct-3-yl]-6-[({[4-methoxy-3-(trifluoromethyl)phenyl]-amino}carbonyl)amino]-1-benzothiophene-2-carboxamide hydrochloride;

N-[(3R)-1-Azabicyclo[2.2.2]oct-3-yl]-6-[({[3-methoxyphenyl]amino}carbonyl)-amino]-1-benzothiophene-2-carboxamide hydrochloride;

N-[(3R)-1-Azabicyclo[2.2.2]oct-3-yl]-6-[({[3-trifluoromethoxyphenyl]amino}-carbonyl)amino]-1-benzothiophene-2-carboxamide hydrochloride;

N-[(3R)-1-Azabicyclo[2.2.2]oct-3-yl]-6-{[(tert-butylamino)carbonyl]amino}-1-benzothiophene-2-carboxamide hydrochloride;

N-[(3R)-1-Azabicyclo[2.2.2]oct-3-yl]-6-{[(cyclohexylamino)carbonyl]amino}-1-benzothiophene-2-carboxamide hydrochloride;

N-[(3R)-1-Azabicyclo[2.2.2]oct-3-yl]-6-[({[(1S)-1-phenylethyl]amino}carbonyl)-amino]-1-benzothiophene-2-carboxamide hydrochloride;

7-[(Anilinocarbonyl)amino]-N-[(3R)-1-azabicyclo[2.2.2]oct-3-yl]-1-benzothiophene-2-carboxamide hydrochloride; and N-[(3R)-1-Azabicyclo[2.2.2]oct-3-yl]-6-({[(4-methoxyphenyl)amino]carbonyl}-amino)-1-benzofuran-2-carboxamide hydrochloride.

24. The method of claim 23, wherein the cognitive impairment is Alzheimer's disease.

25. The method of claim 23, wherein the cognitive impairment is Schizophrenia.

26. The method of claim 23, wherein the method improves perception, concentration, learning, or memory.

* * * * *